US011104952B2

(12) United States Patent
Zai et al.

(10) Patent No.: US 11,104,952 B2
(45) Date of Patent: Aug. 31, 2021

(54) GENETIC MARKERS FOR SUICIDE RISK AND RELATED METHODS

(71) Applicant: Centre for Addiction and Mental Health, Toronto (CA)

(72) Inventors: Clement C. Zai, Toronto (CA); James L. Kennedy, Toronto (CA)

(73) Assignee: Centre for Addiction and Mental Health, Toronto (CA)

( * ) Notice: Subject to any disclaimer, the term of this patent is extended or adjusted under 35 U.S.C. 154(b) by 719 days.

(21) Appl. No.: 15/574,037

(22) PCT Filed: Nov. 19, 2015

(86) PCT No.: PCT/CA2015/051206
§ 371 (c)(1),
(2) Date: Nov. 14, 2017

(87) PCT Pub. No.: WO2016/183659
PCT Pub. Date: Nov. 24, 2016

(65) Prior Publication Data
US 2018/0355431 A1    Dec. 13, 2018

(30) Foreign Application Priority Data

May 15, 2015   (CA) ..................................... 2891830

(51) Int. Cl.
| | |
|---|---|
| *G01N 33/48* | (2006.01) |
| *C12Q 1/6883* | (2018.01) |
| *G16B 30/00* | (2019.01) |
| *G16B 20/00* | (2019.01) |
| *G16B 99/00* | (2019.01) |

(52) U.S. Cl.
CPC ........... *C12Q 1/6883* (2013.01); *G16B 20/00* (2019.02); *G16B 30/00* (2019.02); *G16B 99/00* (2019.02); *C12Q 2600/156* (2013.01); *G01N 2800/30* (2013.01)

(58) Field of Classification Search
None
See application file for complete search history.

(56) References Cited

U.S. PATENT DOCUMENTS

| | | | |
|---|---|---|---|
| 7,906,283 B2 | 3/2011 | McMahon et al. | |
| 10,435,748 B2 | 10/2019 | Zai et al. | |
| 2005/0032678 A1* | 2/2005 | Brennan | C07K 14/705 514/5.3 |
| 2005/0228172 A9 | 10/2005 | Wang | |
| 2006/0024715 A1 | 2/2006 | Liu et al. | |
| 2009/0215852 A1* | 8/2009 | Bascomb | A61K 31/472 514/411 |
| 2017/0002412 A1 | 1/2017 | Zai et al. | |

FOREIGN PATENT DOCUMENTS

| | | |
|---|---|---|
| EP | 2166112 A1 | 3/2010 |
| KR | 1020120038333 A | 4/2012 |
| WO | WO-2010/031712 A2 | 3/2010 |

OTHER PUBLICATIONS

Laje, Gonzalo, et al. "Genome-wide association study of suicidal ideation emerging during citalopram treatment of depressed outpatients." Pharmacogenetics and genomics 19.9 (2009): 666.*
Mullins et al. (Jun. 25, 2014) "Genetic Relationships Between Suicide Attempts, Suicidal Ideation and Major Psychiatric Disorders: A Genomic-Wide Association and Polygenic Scoring Study", American Journal of Medical Genetics Part B, 165B(5):428-437 (3 pages).*
Anonymous (Aug. 1, 2010) "BigDye Terminator vI.1 Cycle Sequencing Kit", http://www3.appliedbiosystems.com/cms/groups/mcbsupport/documents/generaldocuments/cms 041330.pdf, 1-74 (19 pages).*
Anonymous (Oct. 10, 2003) "Reference SNP (refSNP) Cluster Report: rs2491144", https://www.ncbi.nlm.nih. gov/projects/SNP/snp ref.cgi?rs=2491144, 1 page.*
R (Version 3.0.2) (Sep. 25, 2013) "The R Project for Statistical Computing", PCA 5 vars, 1 page.*
Jamain et al. (Aug. 2014) "Common and Rare Variant Analysis in Early-Onset Bipolar Disorder Vulnerability", PLOS One, 9(8): 1-8 (2 pages).*
Willour et al., "Genome-wide association study of attempted suicide." Mol. *Psychiatry*, Apr. 2012, vol. 17(4), pp. 433-444. doi: 10.1038/mp.2011.4. Epub Mar. 22, 2011.
Perroud N, et al., "Genome-wide association study of increasing suicidal ideation during antidepressant treatment in the GENDEP project." *Pharmacogenomics Journal* Feb. 2012;12(1): 68-77. doi: 10.1038/tpj.2010.70. Epub Sep. 28, 2010.
Finseth et al., "Association analysis between suicidal behaviour and candidate genes of bipolar disorder and schizophrenia", *Journal of Affective Disorders*, Jul. 2014, vol. 163, pp. 110-114.
International Search Repoii dated Feb. 22, 2016 for International Application No. PCT/CA2015/051206, filed Nov. 19, 2015, 3 pages.
Perlis et al., "Genome-Wide Association Study of Suicide Attempts in Mood Disorder Patients". *American Journal of Psychiatry*, Dec. 2010, vol. 167(12), pp. 1499-1507.
Schosser et al, "Genornewide Association Scan of Suicidal Thoughts and Behaviour in Major Depression". *PLoS One*, Jul. 5, 2011, vol. 6(7), e20690, pp. 1-10.
Zai et al., "A genome-wide association study of suicide severity scores in bipolar disorder". *Journal of Psychiatric Research*, Nov. 20, 2014, vol. 65, pp. 23-29.
Extended European Search Report dated Aug. 24, 2018 for European Application No. EP-15892076.9, filed Nov. 19, 2015. (8 pages).
Chaimowitz, G., Psychotherapy in Psychiatry, The Canadian Journal of Psychiatry, vol. 49, No. 2, 2003 (4 pgs.).
Dayan et al., Noninvasive brain stimulation: from physiology to network dynamics and back, Nat Neurosci Jul. 2013; 16(7): 838-844.

(Continued)

*Primary Examiner* — Anna Skibinsky
(74) *Attorney, Agent, or Firm* — Muriel Liberto, Esq.; Mintz Levin Cohn Ferris Glovsky and Popeo, P.C.

(57) ABSTRACT

The invention provides genetic markers of severe suicidal behavior, related compositions, computer systems, and methods.

14 Claims, 15 Drawing Sheets

Specification includes a Sequence Listing.

(56) References Cited

OTHER PUBLICATIONS

George et al., The Expanding Evidence Base for rTMS Treatment of Depression, Curr Opin Psychiatry. Jan. 2013; 26(1): 13-18.

Anonymous (Aug. 1, 2010) "BigDye Terminator v1.1 Cycle Sequencing Kit", http://www3.appliedbiosystems.com/cms/groups/mcbsupport/documents/generaldocuments/cms 041330.pdf, 1-74 (19 pages).

Purcell et al. (2007) "Plink: A Tool Set for Whole-genome Association and Population-Based Linkage Analyses", American Journal of Human Genetics, 81(3):559-75.

Scott et al. (May 5, 2009) "Genome-wide association and meta-analysis of bipolar disorder in individuals of European ancestry", Proceedings of the National Academy of Sciences, 106(18):7501-7506.

\* cited by examiner

SEQUENCE LISTING

<160> NUMBER OF SEQ ID NOS: 11

<210> SEQ ID NO 1
<211> LENGTH: 51
<212> TYPE: DNA
<213> ORGANISM: Homo sapiens
<220> FEATURE:
<221> NAME/KEY: variation
<222> LOCATION: (26)..(26)
<223> OTHER INFORMATION: rs2610025, m is A or C.

<400> SEQUENCE: 1
actcatttgg cttaaaattt tatttmctaa ttttgcagaa tgacccttag g          51

<210> SEQ ID NO 2
<211> LENGTH: 51
<212> TYPE: DNA
<213> ORGANISM: Homo sapiens
<220> FEATURE:
<221> NAME/KEY: variation
<222> LOCATION: (26)..(26)
<223> OTHER INFORMATION: rs10448044, y is C or T.

<400> SEQUENCE: 2
cagccaccgc tggacaaaga atggaygtgg ccacaggaac tgctgccact a          51

<210> SEQ ID NO 3
<211> LENGTH: 51
<212> TYPE: DNA
<213> ORGANISM: Homo sapiens
<220> FEATURE:
<221> NAME/KEY: variation
<222> LOCATION: (26)..(26)
<223> OTHER INFORMATION: rs7079041, r is A or G.

<400> SEQUENCE: 3
agaacagtgg atattggtga tcagcraatg ttgctgcctg atcgttcctc t          51

<210> SEQ ID NO 4
<211> LENGTH: 51
<212> TYPE: DNA
<213> ORGANISM: Homo sapiens
<220> FEATURE:
<221> NAME/KEY: variation
<222> LOCATION: (26)..(26)
<223> OTHER INFORMATION: rs720903, w is A or T.
<220> FEATURE:
<221> NAME/KEY: variation
<222> LOCATION: (26)..(26)
<223> OTHER INFORMATION: rs720903, w is A or T.

<400> SEQUENCE: 4
acccttgcct cccaaagtgt tgagawtatg agcgtgagcc accatgccca g          51

<210> SEQ ID NO 5
<211> LENGTH: 51
<212> TYPE: DNA
<213> ORGANISM: Homo sapiens
<220> FEATURE:
<221> NAME/KEY: variation
<222> LOCATION: (26)..(26)
<223> OTHER INFORMATION: rs10483836, k is G or T.

<400> SEQUENCE: 5
tataatttga tcctttagtt gtattktgat gatcacttgg aataacattc a          51

<210> SEQ ID NO 6
<211> LENGTH: 51

```
<212> TYPE: DNA
<213> ORGANISM: Homo sapiens
<220> FEATURE:
<221> NAME/KEY: variation
<222> LOCATION: (26)..(26)
<223> OTHER INFORMATION: rs7244261, y is C or T.
<220> FEATURE:
<221> NAME/KEY: variation
<222> LOCATION: (26)..(26)
<223> OTHER INFORMATION: rs7244261, y is C or T.

<400> SEQUENCE: 6
taaaataact caggtatttt aaaatycaaa ataaaatata atctctcaat t            51

<210> SEQ ID NO 7
<211> LENGTH: 51
<212> TYPE: DNA
<213> ORGANISM: Homo sapiens
<220> FEATURE:
<221> NAME/KEY: variation
<222> LOCATION: (26)..(26)
<223> OTHER INFORMATION: rs2491144, r is A or G.

<400> SEQUENCE: 7
caagttcctt ctgtcttgtt aagctrttgt cattccgtgt tgccctcatt c            51

<210> SEQ ID NO 8
<211> LENGTH: 51
<212> TYPE: DNA
<213> ORGANISM: Homo sapiens
<220> FEATURE:
<221> NAME/KEY: variation
<222> LOCATION: (26)..(26)
<223> OTHER INFORMATION: rs9315639, y is C or T.
<220> FEATURE:
<221> NAME/KEY: variation
<222> LOCATION: (26)..(26)
<223> OTHER INFORMATION: rs9315639, y is C or T.

<400> SEQUENCE: 8
catgctacag tcacctaaaa cctgtyctgg cttggataga atatcttccc a            51

<210> SEQ ID NO 9
<211> LENGTH: 51
<212> TYPE: DNA
<213> ORGANISM: Homo sapiens
<220> FEATURE:
<221> NAME/KEY: variation
<222> LOCATION: (26)..(26)
<223> OTHER INFORMATION: rs11082138, y is C or T.

<400> SEQUENCE: 9
gtatttgtat tcaatctcca cttcaytgga aacttcttga ggacaaatgt g            51

<210> SEQ ID NO 10
<211> LENGTH: 51
<212> TYPE: DNA
<213> ORGANISM: Homo sapiens
<220> FEATURE:
<221> NAME/KEY: variation
<222> LOCATION: (26)..(26)
<223> OTHER INFORMATION: rs11697517, y is C or T.

<400> SEQUENCE: 10
atactaaatg ttaacttctg caagtycctt ttctcactca acattactgt a            51

<210> SEQ ID NO 11
<211> LENGTH: 51
<212> TYPE: DNA
```

```
<213> ORGANISM: Homo sapiens
<220> FEATURE:
<221> NAME/KEY: variation
<222> LOCATION: (26)..(26)
<223> OTHER INFORMATION: rs2186437, m is A or C.
<220> FEATURE:
<221> NAME/KEY: variation
<222> LOCATION: (26)..(26)
<223> OTHER INFORMATION: rs2186437, m is A or C.

<400> SEQUENCE: 11
caggctggaa tgcagtggtg tcaacmtatc tccttttagc cttgaactcc t        51
```

GENETIC MARKERS FOR SUICIDE RISK AND RELATED METHODS

RELATED APPLICATIONS

This application is a national stage entry, filed under 35 U.S.C. § 371, of International Application No, PCT/CA2015/051206, filed on Nov. 19, 2015, which claims priority to Canadian Patent Application No. 2,891,830, filed on May 15, 2015, the contents of which are hereby fully incorporated by reference in their entireties.

SEQUENCE LISTING

The instant application contains a Sequence Listing which has been submitted electronically in ASCII format and is hereby incorporated by reference in its entirety. Said ASCII copy, created on Feb. 6, 2018, is named 052237-504N01US_ST25.txt and is 3,084 bytes in size.

FIELD OF THE DISCLOSURE

The present invention relates to genetic markers of suicide risk and related computer systems, compositions and methods.

BACKGROUND OF THE DISCLOSURE

Suicide claims one million lives worldwide annually, and for each completed suicide, there are twenty suicide attempts, making it a serious public health concern. Over 90% of suicide victims have at least one psychiatric diagnosis, including bipolar disorder (BD), where as much as 8% of BD followed for up to 40 years committed suicide. Suicide has a prominent genetic component, as evidenced by the observation that suicide attempts tend to occur more often within families and there is greater concordance between monozygotic twins than between dizygotic twins where the concordant phenotype includes both completed and attempted suicides. A review of twin studies estimated the heritability of suicidal behavior to be up to 55% (Voracek & Loibl, 2007).

A number of linkage studies have been conducted on suicide starting in 2004 with those of Zubenko and co workers. Their findings on the short arm of chromosome 2 were later replicated in 162 BD families (Willour et al, 2007), and more recently confirmed in the regional linkage study meta-analysis of 2p12 (Butler et al, 2010).

Recent technological advances have permitted the high-throughput genotyping of hundreds of thousands of single-nucleotide polymorphisms across the genome. While no genome-wide significant (defined as having a significance level of less than $5\times10^{-8}$) findings have been reported to date, a number of suggestive findings have emerged (Perroud et al, 2011; Schosser et al, 2011). For example, recently, a genome-wide association study (GWAS) was reported on samples of 2,698 BD patients of which 1,201 had a previous suicide attempt. After meta-analysis of markers with $p<1\times 10^{-3}$ from their discovery sample (GAIN, TGEN, German) with their replication BD sample (STEP-BD, WTCCC, UCL), the most significantly associated marker was rs300774 in an intergenic region at chromosomal region 2p25, which contains the SH3YL1, ACP1, and FAM150B genes. The association finding was supported by post-mortem prefrontal cortical gene expression analysis, where suicide completers were found to have significantly higher ACP1 expression than non-suicide victims (Willour et al, 2012). The strongest association signal from another report of a GWAS of suicide attempt on the BD sample (STEP-BD, WTCCC, UCL) came from the intergenic chromosome 10 marker rs1466846, but this finding was not replicated in the replication sample (GAIN, TGEN, German) (Perlis et al, 2010).

Part of the reason for both lack of a strong association signal and robust replication could be that the samples are underpowered for analysis due to dichotomizing of the suicide attempt as the outcome variable. A GWAS on suicidality scores, which are derived from the Schedule for Clinical Assessment in Neuropsychiatry (SCAN) interview, was conducted with a major depression sample from the RADIANT study (Schosser et al, 2011). The suicidality score captures suicide severity from suicide ideation to attempt. As such, there is a need to identify additional genetic risk factors for suicide.

SUMMARY OF THE DISCLOSURE

The present invention is based upon the discovery of new genetic markers associating with a higher risk of severe suicidal behavior in a genome wide association studies involving a large sample of BD patients and in a GWAS of suicide attempt in BD patients. The present inventors identified a number of markers and panels of markers that contribute to the risk of severe suicidal behavior and are therefore useful in methods and compositions for identifying at-risk individuals, as described in detail infra.

The invention provides methods, including computer implemented methods and computer systems adapted and designed to implement the methods, for identifying a subject at risk of severe suicidal behavior (SSB). In one embodiment, the methods comprise determining or receiving the subject's genotype for a plurality of single nucleotide polymorphisms (SNPs), the plurality consisting of two or more, three or more, or four or more, of the SNPs identified in Table 1; or the plurality consists of each SNP in at least one of the panels of SNPs identified in Table 2. In one embodiment, the plurality of SNPs comprises or consists of markers F and H (as identified in Table 8). In one embodiment, the methods of the invention comprise determining or receiving a subject's genotype for at least three SNPs selected from the SNPs listed in Table 1. In one embodiment, the at least three SNPs comprises markers F, H, and either I or K, or both (as identified in Table 8).

In embodiments, the plurality of two or more SNPs comprises G or H. In embodiments, the plurality of two or more SNPs consists of G and H. In embodiments, the plurality further comprises I or K.

In one embodiment, the methods comprise determining or receiving the subject's genotype for a plurality of single nucleotide polymorphisms (SNPs), the plurality consisting of each SNP in at least one of the panels of SNPs identified in Table 2. In one embodiment, the panel is selected from a panel that accounts for al least 5% of the variance in risk for SSB, e.g., a panel selected from panels 1-17, and 19-22 in Table 2. In one embodiment, the panel is selected from a panel that accounts for at least 6% of the variance in risk for SSB, e.g., a panel selected from panels 1, 3-5, 7-17, and 19-22 in Table 2. In one embodiment, the panel is selected from a panel that accounts for at least 7% of the variance in risk for SSB, e.g., a panel selected from panels 1, 3-5, 9-11, 13, 14, 16, 17 and 19-22 in Table 2. In one embodiment, the panel is selected from a panel that accounts for at least 8% of the variance in risk for SSB, e.g., a panel selected from panels 3-5, 9-11, 13, 14, 20 and 22 in Table 2. In one embodiment, the panel is selected from a panel that accounts for at least 9% of the variance in risk for SSB. e.g., a panel selected from panels 4, 9, 13, 20 and 22 in Table 2.

In embodiments, the panel is selected from panel 2, 9, 15, 17, 19 and 20 in Table 2.

The methods further comprise assigning a genetic risk score to each genotype of the plurality of SNPs and generating a total genetic risk score for the subject based on the sum of the genetic risk scores of the plurality of SNPs. The total genetic risk score for the subject is used, either alone, or in combination with one or more additional features (also referred to as data attributes) to classify the subject according to risk of SSB, for example into one of a "low", "intermediate", or "high" risk group. Thus, the methods further comprise generating an SSB risk assessment for the subject using one or more data attributes including at least the subject's total genetic risk score. The one or more data attributes (other than total genetic risk score) may include one or more of the subject's diagnosis, concomitant medications, comorbidities, age, gender, ethnicity, stressful life events, childhood trauma, alcohol use, use of controlled substances, and use of psychotropic agents. In one embodiment, the SSB risk assessment is selected from low, intermediate, or high. In one embodiment, a genotype risk score of greater than 1.5 is classified as intermediate or high risk for SSB. In one embodiment, a genotype risk score of between 1.5 and 2.5 is classified as high risk for SSB. In one embodiment, a genotype risk score of at least 1.5, at least 2.0, at least 2.5, or at least 3.0 is classified as high risk for SSB. In embodiments, a genotype risk score of 2.0 or more is classified as high risk for SSB. In one embodiment, a genotype risk score of between 1.5 and 4.0, or between 2.0 and 4.0, or between 2.5 and 4.0, or between 3.0 and 4.0 is classified as being high risk for SSB. In one embodiment, a genotype risk score of 1.5 or less is classified as low risk for SSB. In one embodiment, a genotype risk score of between 0.5 and 1.5 or 2.0 is classified as intermediate risk for SSB.

The methods may further comprise outputting an indication of the subject's SSB risk assessment. The indication may be an audio, visual or textual indication, or any combination of the foregoing. In one embodiment, the outputting is to a graphical user interface (GLU). In one embodiment, the methods further comprise outputting a recommended course of action based upon the subject's SSB risk assessment including proposed therapies and/or interventions tailored to the patient's risk. For example, for individuals identified as being at intermediate risk for SSB, interventions would include more frequent visits and monitoring, medication adjustments, augmentation with other therapies (including but not limited to psychotherapies, cognitive behavioral therapy, and brain stimulation). For individuals identified as being at high risk for SSB, in addition to interventions considered for intermediate-risk individuals, hospitalization that might include higher levels of observations would be contemplated. Treating physicians would also advise family members and alert other caregivers (for example, community nurses, social workers, and mental health workers) to increase vigilance for these high-risk individuals.

In one embodiment, the subject's genotype is received directly from equipment used to determine the genotype or the subject's genotype is input by a user. In one embodiment, the determining step is performed in vitro. In one embodiment, the methods further comprise obtaining a biological sample from the subject prior to the determining step. The biological sample may be any suitable biological sample for extracting the subject's DNA. In one embodiment, the biological sample is blood or saliva.

In one embodiment, the methods further comprise receiving input regarding one or more patient-specific data attributes including or selected from one or more of diagnosis, concomitant medications, comorbidities, age, gender, ethnicity, stressful life events, childhood trauma, alcohol use, use of controlled substances, and use of psychotropic agents. In one embodiment, the one or more patient-specific data attributes is received directly from equipment used to extract the data from an electronic record, such as an electronic health record. In one embodiment, the one or more patient-specific data attributes is input by a user.

The invention also provides an in vitro diagnostic method for assessing whether a subject is at increased risk of severe suicidal behavior (SSB) compared to the general population, the method comprising determining, in vitro, or receiving, the subject's genotype for a plurality of single nucleotide polymorphisms (SNPs), the plurality consisting of two or more of the SNPs identified in Table 1, or each SNP in at least one of the panels of SNPs identified in Table 2. The method may further comprise assigning a genetic risk score to each genotype of the plurality of SNPs; generating a total genetic risk score for the subject based on the sum of the genetic risk scores of the plurality of SNPs; and generating an SSB risk assessment for the subject using one or more data attributes including at least the subject's total genetic risk score. Further data attributes that may be used are as discussed above.

The invention also provides a kit of parts comprising a set of nucleotides in the form of primers suitable for amplifying, or in the form of probes suitable for identifying, a plurality of single nucleotide polymorphisms (SNPs), the plurality consisting of two or more of the SNPs identified in Table 1, or each SNP in at least one of the panels of SNPs identified in Table 2.

The invention also provides a non-transitory computer readable medium containing executable instructions that when executed by at least one programmable processor, cause the at least one programmable processor to perform operations comprising the methods, or one or more steps of the methods, described above, e.g., receiving a subject's genotype for a plurality of single nucleotide polymorphisms (SNPs), the plurality consisting of two or more of the SNPs identified in Table 1, or each SNP in at least one of the panels of SNPs identified in Table 2, assigning a genetic risk score to each genotype of the plurality of SNPs, generating a total genetic risk score for the subject based on the sum of the genetic risk scores of the plurality of SNPs, generating an SSB risk assessment for the subject using one or more data attributes including at least the subject's total genetic risk score, and outputting an indication of the subject's SSB risk assessment.

The invention also provides a system for identifying a subject at risk of severe suicidal behavior (SSB), the system comprising a Genetic Risk Score Generator, a Risk Assessment Generator, and at least one data processor configured to perform the methods, or one or more steps of the methods, described above. In one embodiment, the system is configured to receive a subject's genetic data from genotype determining equipment. In one embodiment, the system is configured to receive from an electronic health record one or more data attributes in addition to the subject's genetic data. In one embodiment, the system further comprises a natural language processing component. In one embodiment, the system further comprises a graphical user interface for receiving input regarding one or more patient-specific data attributes including or selected from one or more of diagnosis, concomitant medications, comorbidities, age, gender, ethnicity, stressful life events, childhood trauma, alcohol use, use of controlled substances, and use of psychotropic agents.

DETAILED DESCRIPTION OF THE DISCLOSURE

Figure 1:
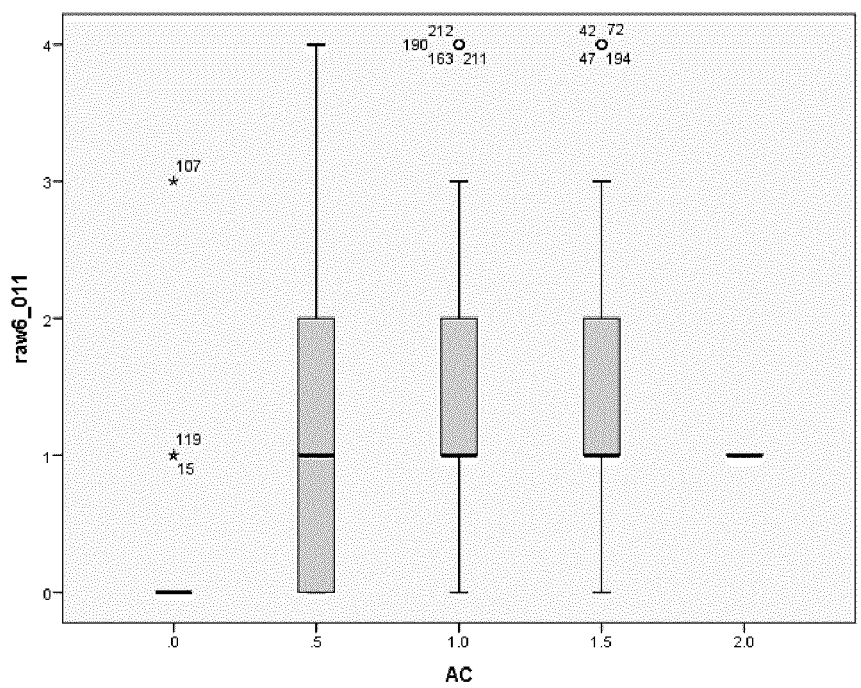
FIG. 1: Boxplot showing raw suicide severity scones (y-axis) across the additive genotype risk scores (x-axis) for markers AC (as identified in Table 8).
Figure 2:
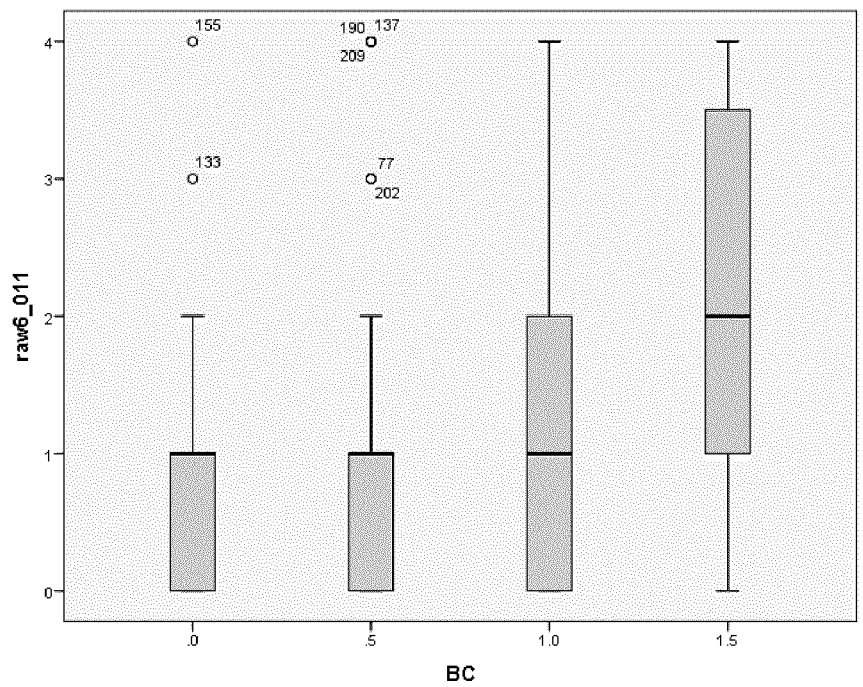
FIG. 2: Boxplot showing raw suicide severity scores (y-axis) across the additive genotype risk scores (x-axis) for markers BC (as identified in Table 8).
Figure 3:
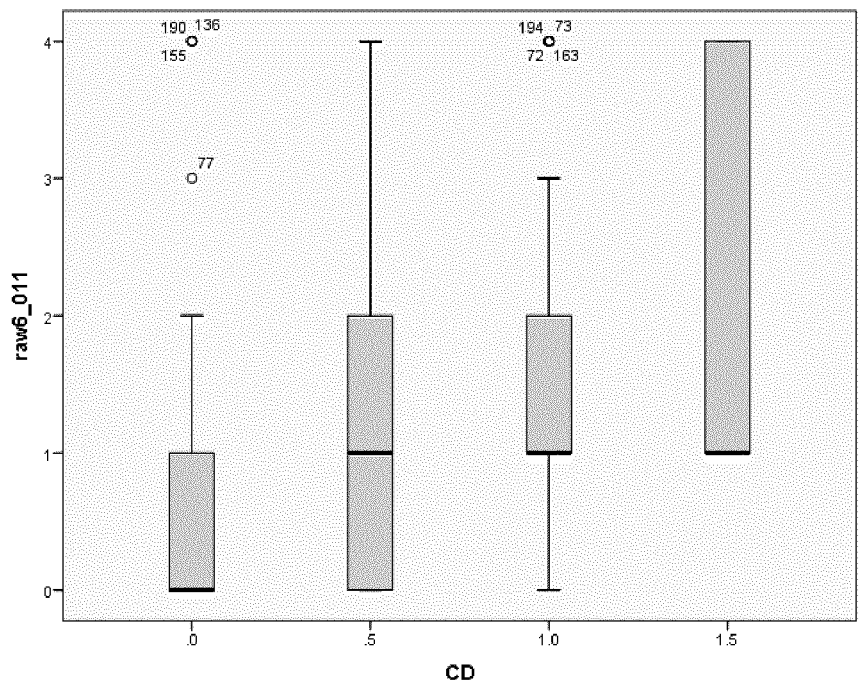
FIG. 3: Boxplot showing raw suicide severity scores (y-axis) across the additive genotype risk scores (x-axis) for markers CD (as identified in Table 8).
Figure 4:
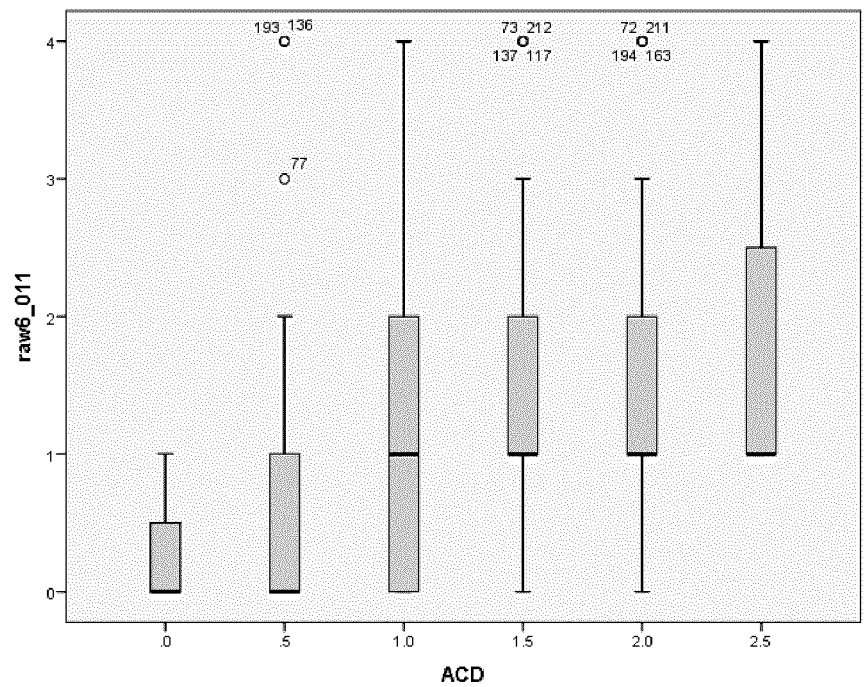
FIG. 4: Boxplot showing raw suicide severity scores (y-axis) across the additive genotype risk scores (x-axis) for markers ACD (as identified in Table 8).
Figure 5:
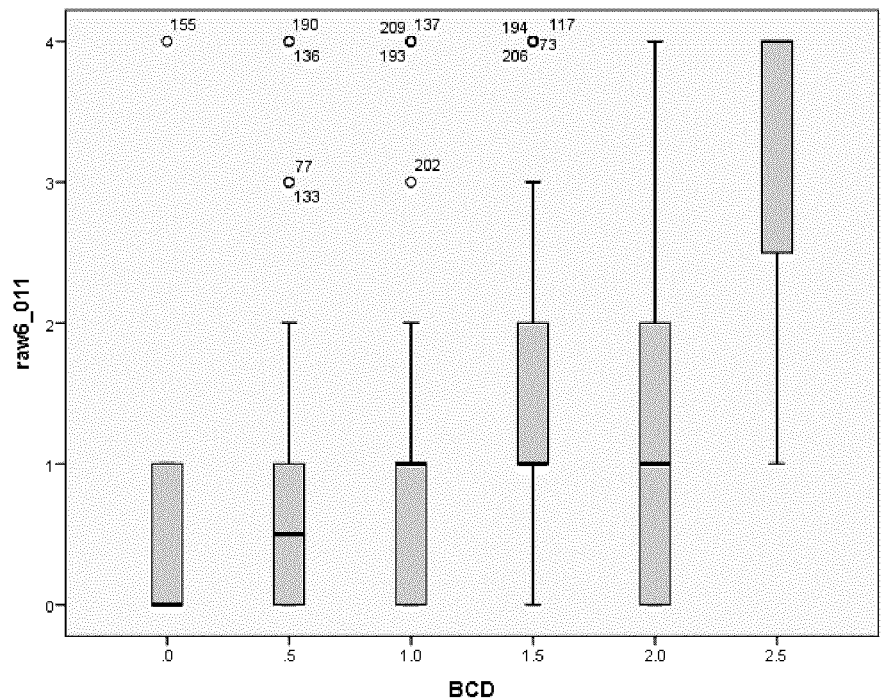
FIG. 5: Boxplot showing raw suicide severity scores (y-axis) across the additive genotype risk scores (x-axis) for markers BCD (as identified in Table 8).
Figure 6:
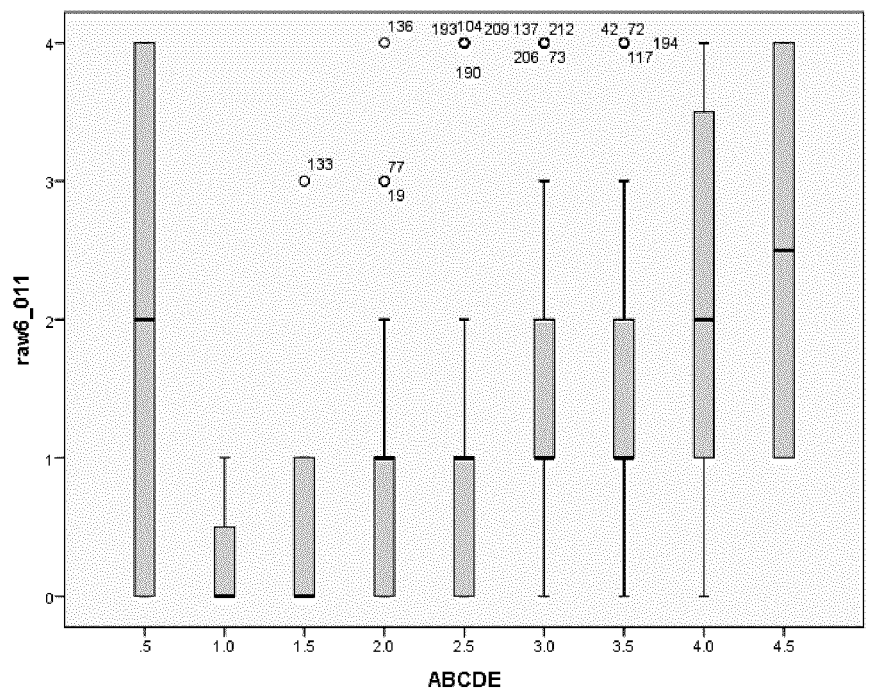
FIG. 6: Boxplot showing raw suicide severity scores (y-axis) across the additive genotype risk scores (x-axis) for markers ABCDE (as identified in Table 8).
Figure 7:
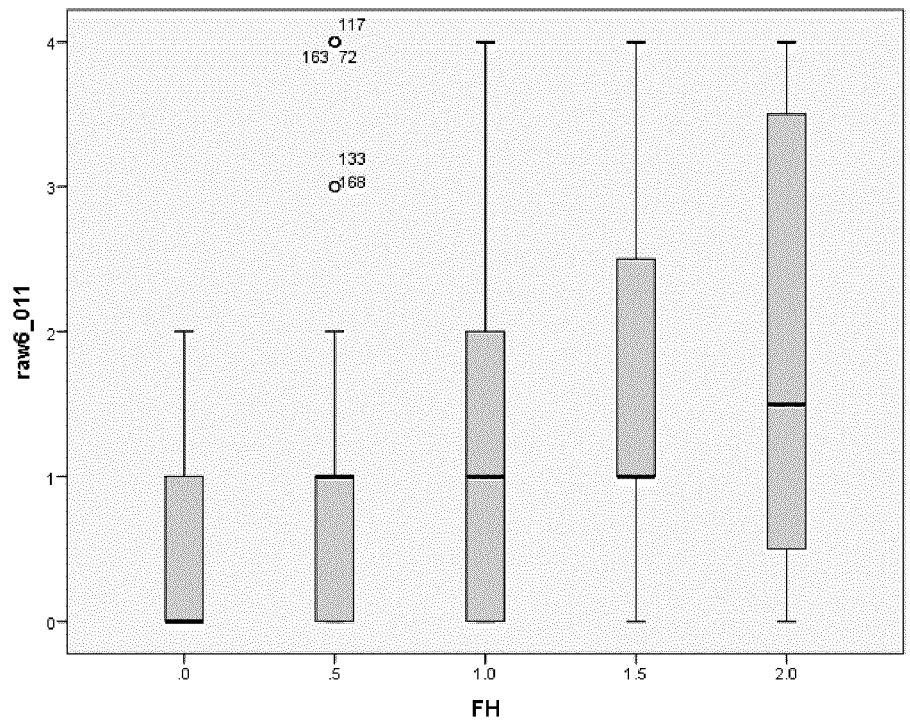
FIG. 7: Boxplot showing raw suicide severity scores (y-axis) across the additive genotype risk scores (x-axis) for markers FH (as identified in Table 8).
Figure 8:
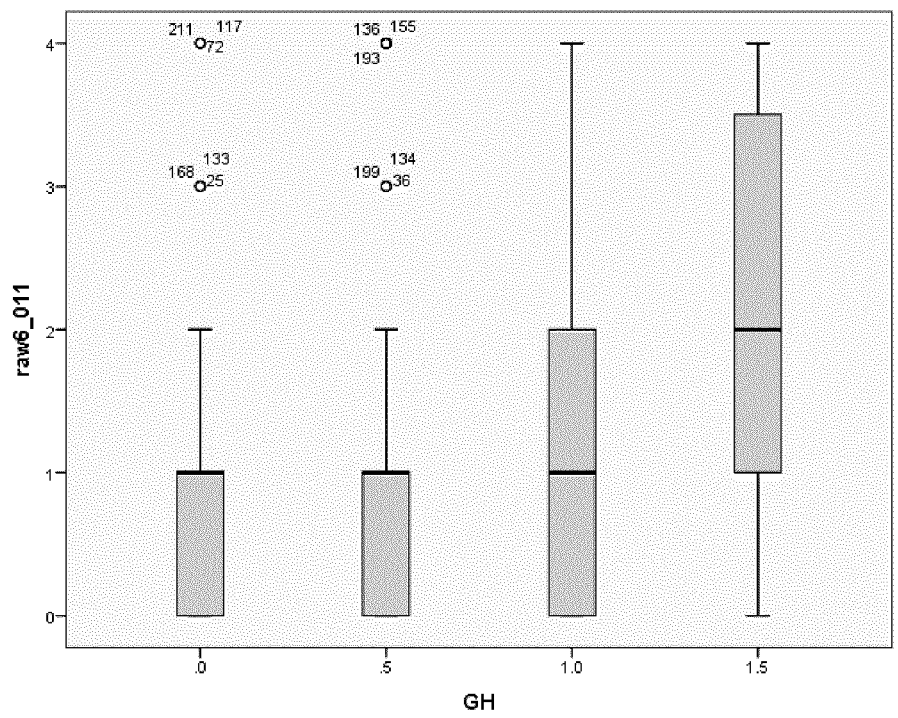
FIG. 8: Boxplot showing raw suicide severity scores (y-axis) across the additive genotype risk scores (x-axis) for markers GH (as identified in Table 8).
Figure 9:
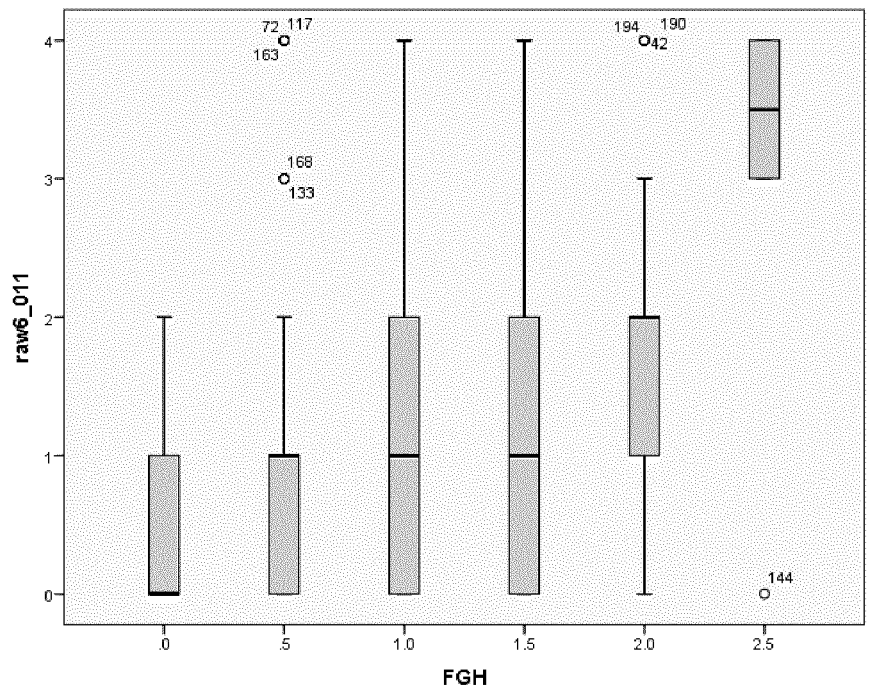
FIG. 9: Boxplot showing raw suicide severity scores (y-axis) across the additive genotype risk scores (x-axis) for markers FGH (as identified in Table 8).
Figure 10:
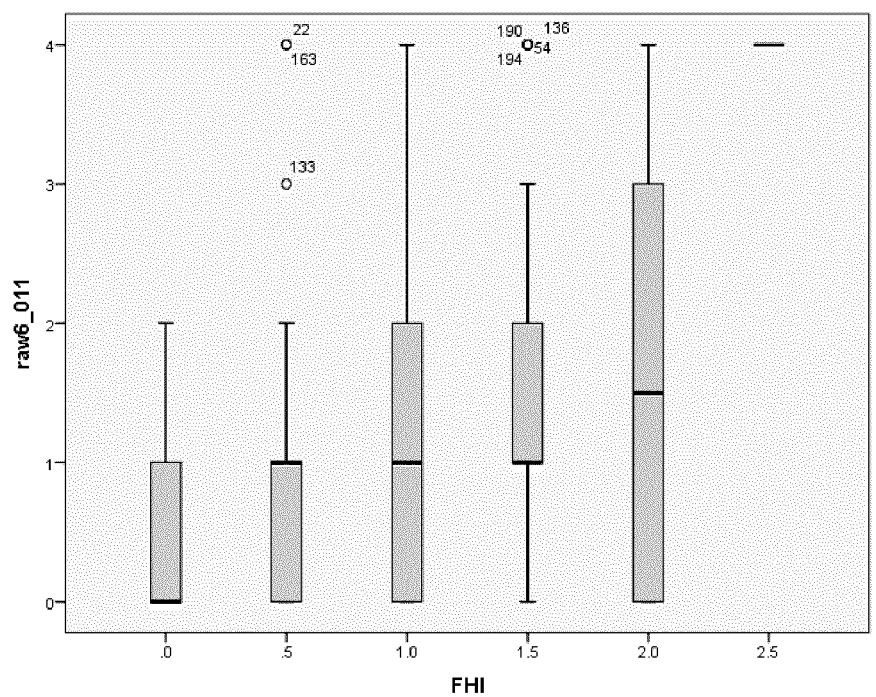
FIG. 10: Boxplot showing raw suicide severity scores (y-axis) across the additive genotype risk scores (x-axis) for markers FHI (as identified in Table 8).
Figure 11:
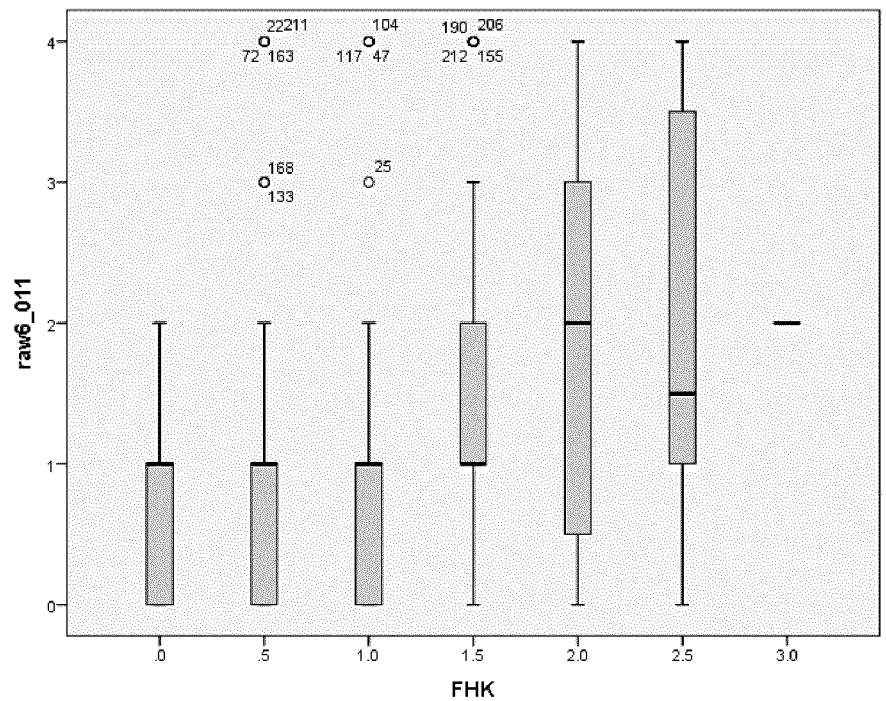
FIG. 11: Boxplot showing raw suicide severity scores (y-axis) across the additive genotype risk scores (x-axis) for markers FHK (as identified in Table 8).
Figure 12:
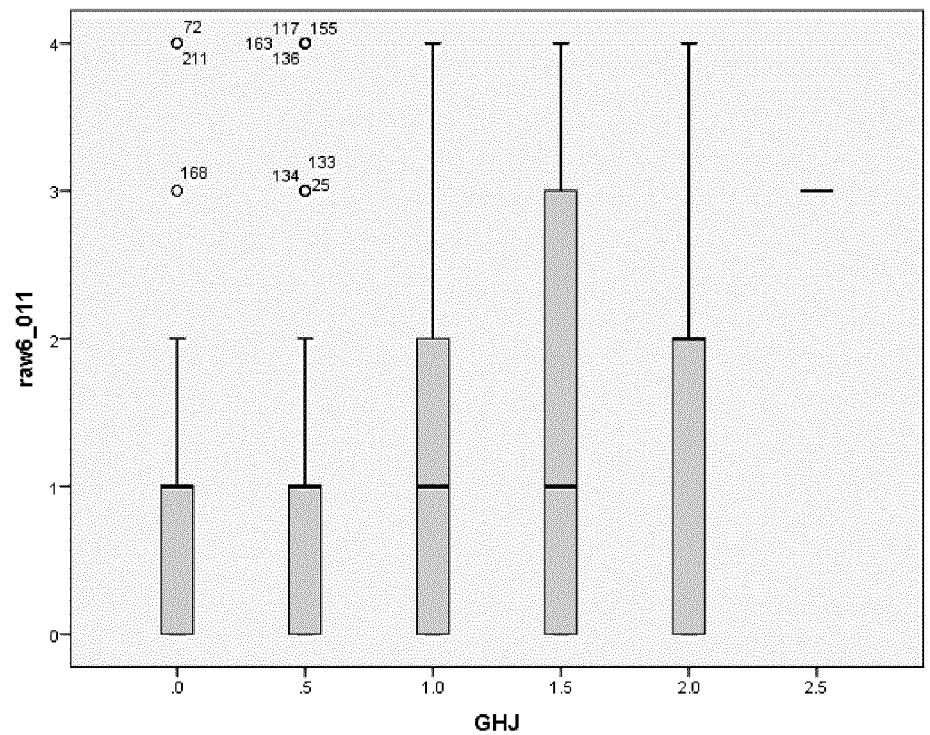
FIG. 12: Boxplot showing raw suicide severity scores (y-axis) across the additive genotype risk scores (x-axis) for markers GHJ (as identified in Table 8).
Figure 13:
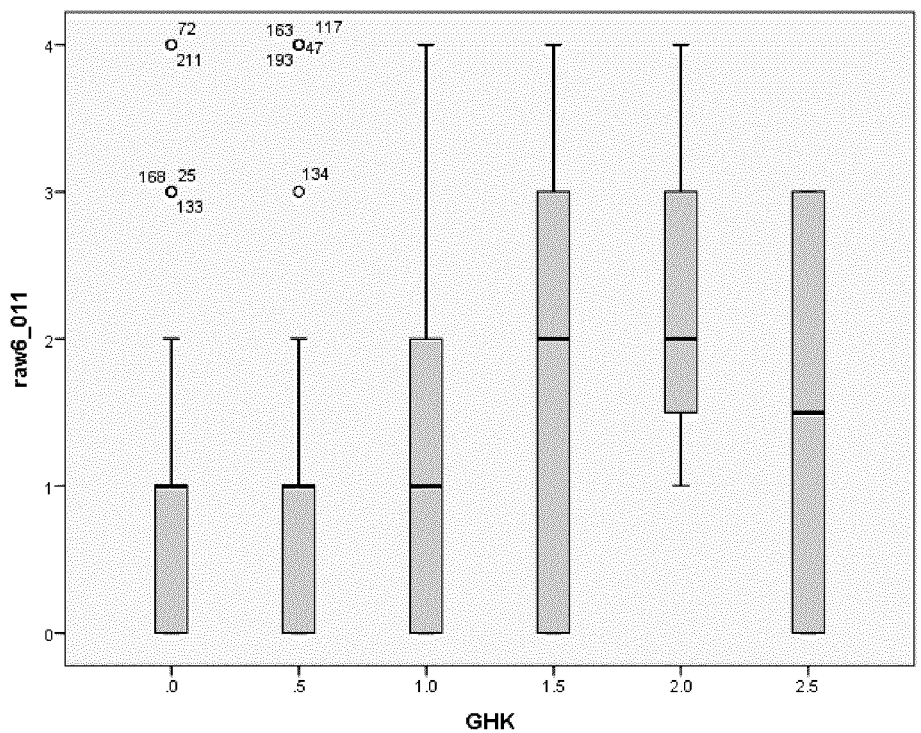
FIG. 13: Boxplot showing raw suicide severity scores (y-axis) across the additive genotype risk scores (x-axis) for markers GHK (as identified in Table 8).
Figure 14:
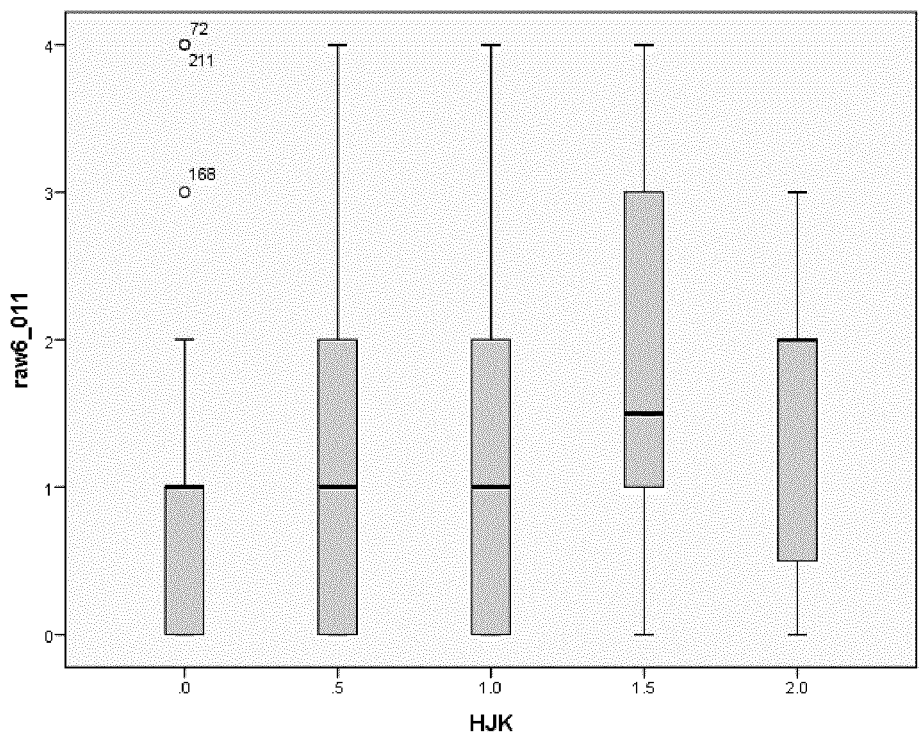
FIG. 14: Boxplot showing raw suicide severity scores (y-axis) across the additive genotype risk scores (x-axis) for markers HJK (as identified in Table 8).
Figure 15:
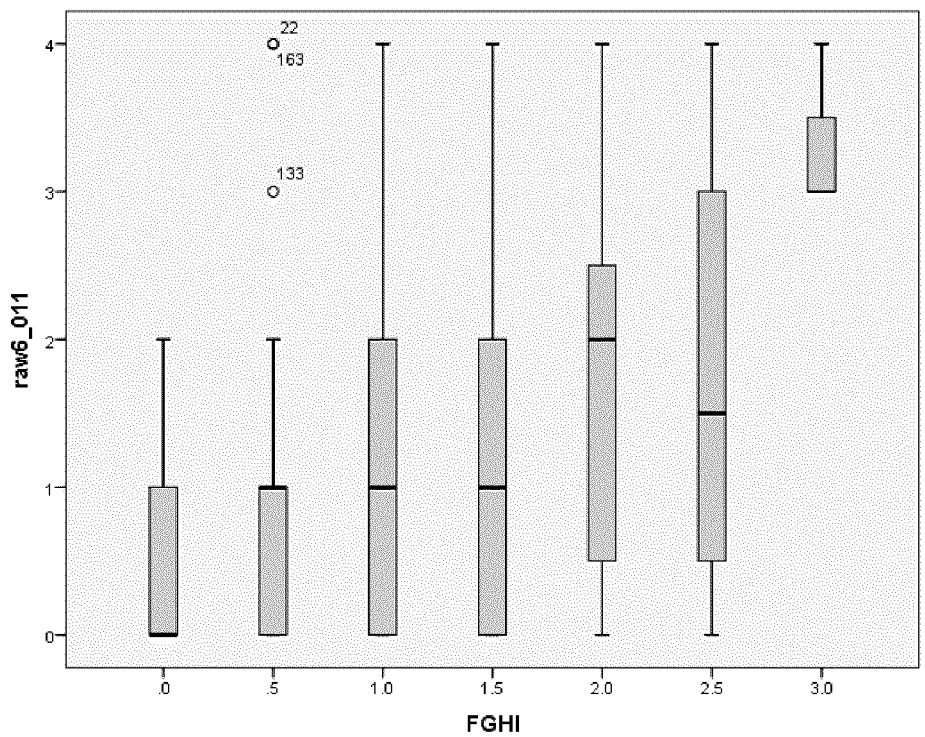
FIG. 15: Boxplot showing raw suicide severity scores (y-axis) across the additive genotype risk scores (x-axis) for markers FGHI (as identified in Table 8).
Figure 16:
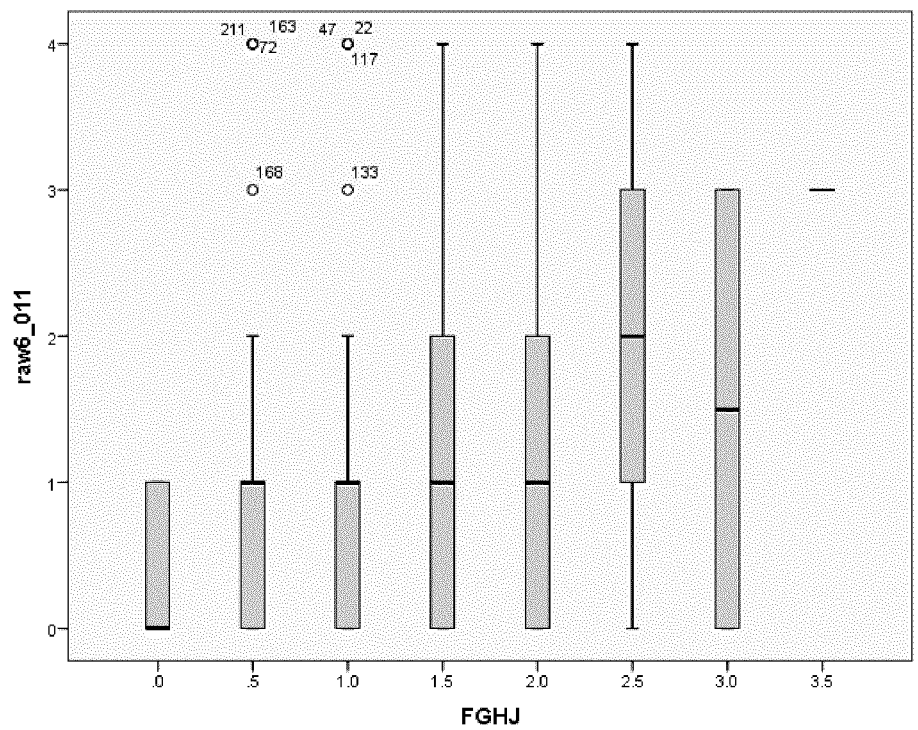
FIG. 16: Boxplot showing raw suicide severity scores (y-axis) across the additive genotypic risk scores (x-axis) for markers FGHJ (as identified in Table 8).
Figure 17:
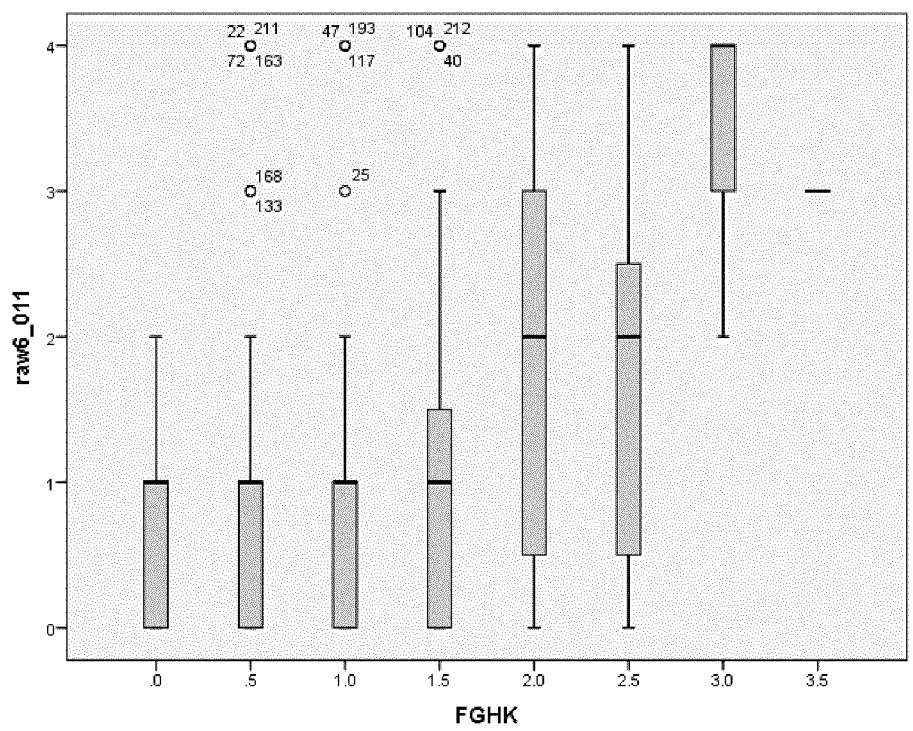
FIG. 17: Boxplot showing raw suicide severity scores (y-axis) across the additive genotypic risk scores (x-axis) for markers FGHK (as identified in Table 8).
Figure 18:
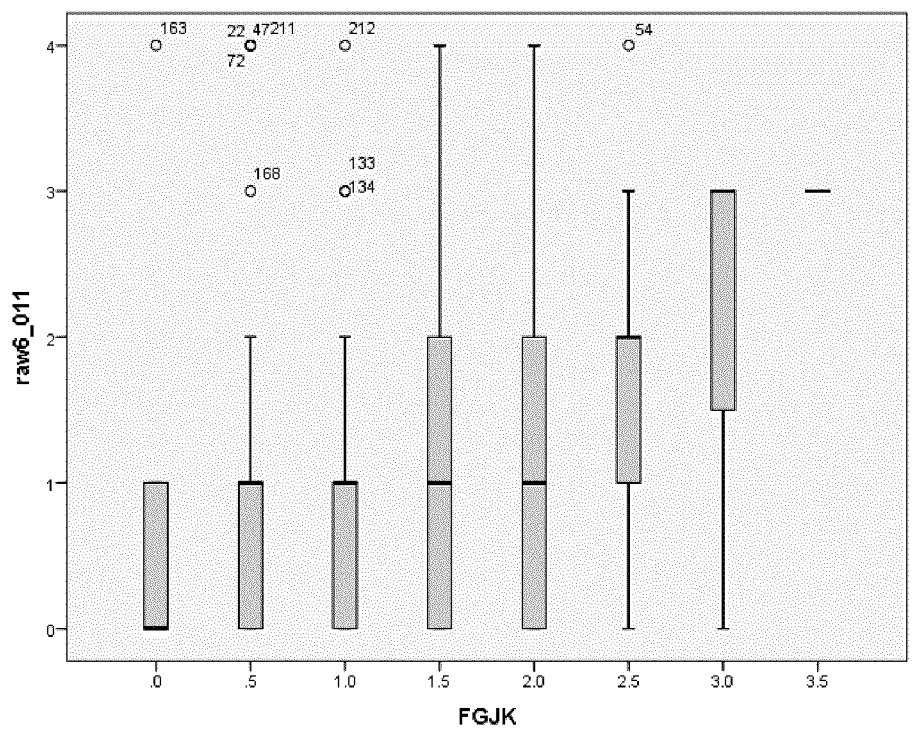
FIG. 18: Boxplot showing raw suicide severity scores (y-axis) across the additive genotypic risk scores (x-axis) for markers FGJK (as identified in Table 8).
Figure 19:
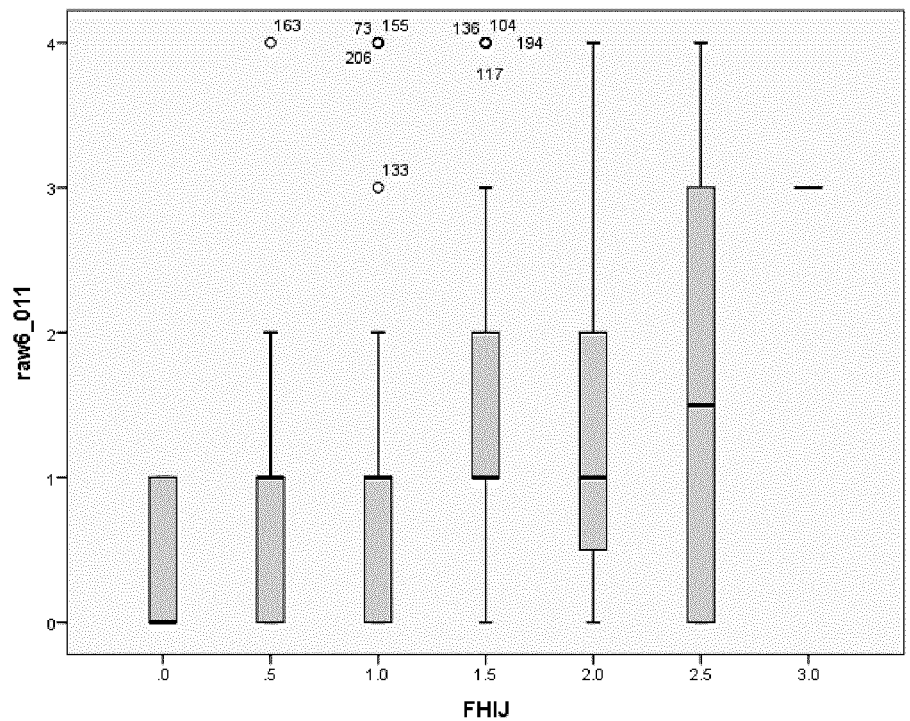
FIG. 19: Boxplot showing raw suicide severity scores (y-axis) across the additive genotype risk scores (x-axis) for markers FHIJ (as identified in Table 8).
Figure 20:
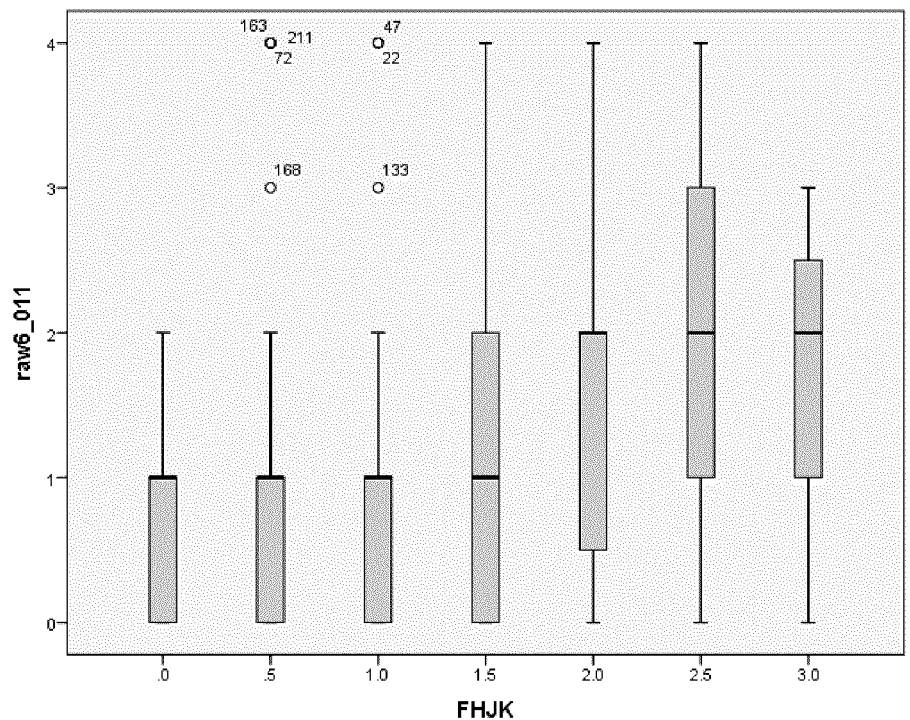
FIG. 20: Boxplot showing raw suicide severity scores (y-axis) across the additive genotypic risk scores (x-axis) for markers FHJK (as identified in Table 8).
Figure 21:
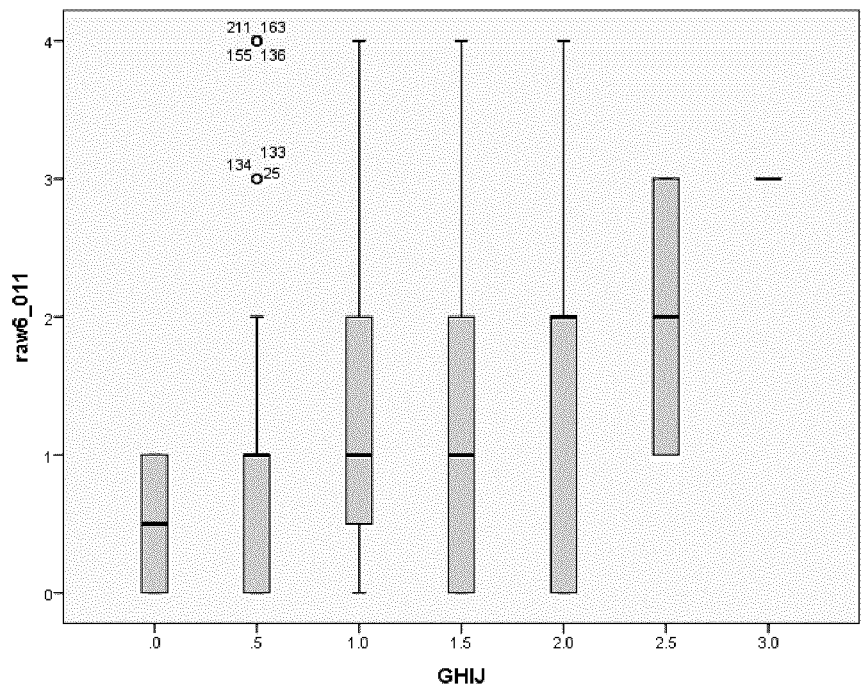
FIG. 21: Boxplot showing raw suicide severity scores (y-axis) across the additive genotypic risk scores (x-axis) for markers GHIJ (as identified in Table 8).
Figure 22:
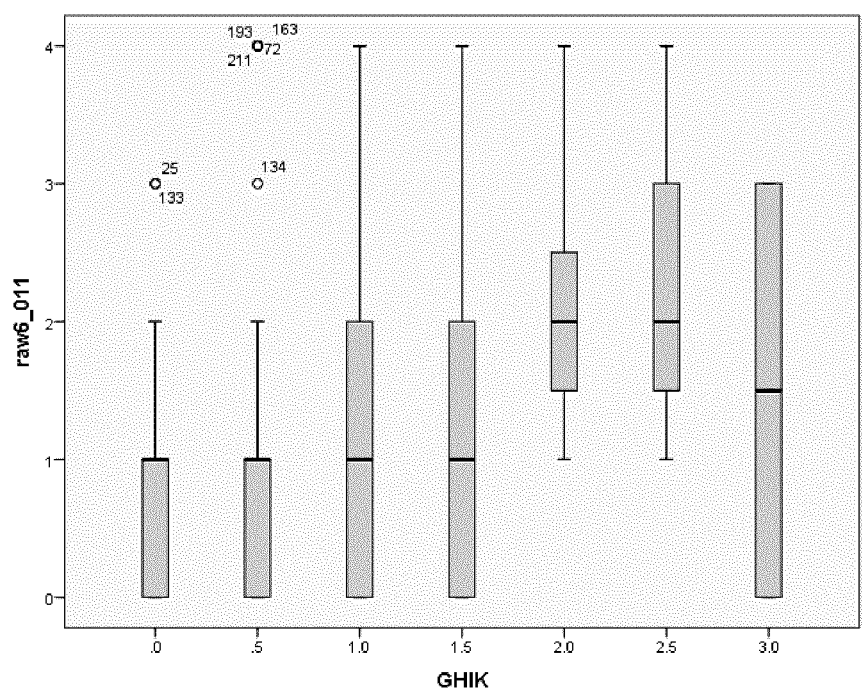
FIG. 22: Boxplot showing raw suicide severity scores (y-axis) across the additive genotypic risk scores (x-axis) for markers GHIK (as identified in Table 8).
Figure 23:
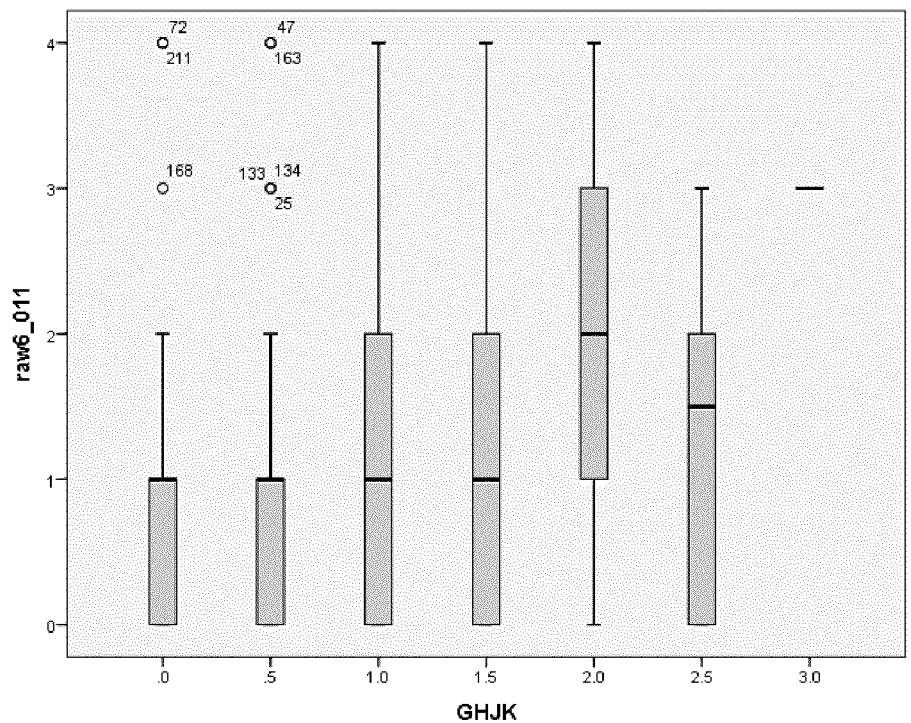
FIG. 23: Boxplot showing raw suicide severity scores (y-axis) across the additive genotype risk scores (x-axis) for markers GHJK (as identified in Table 8).
Figure 24:
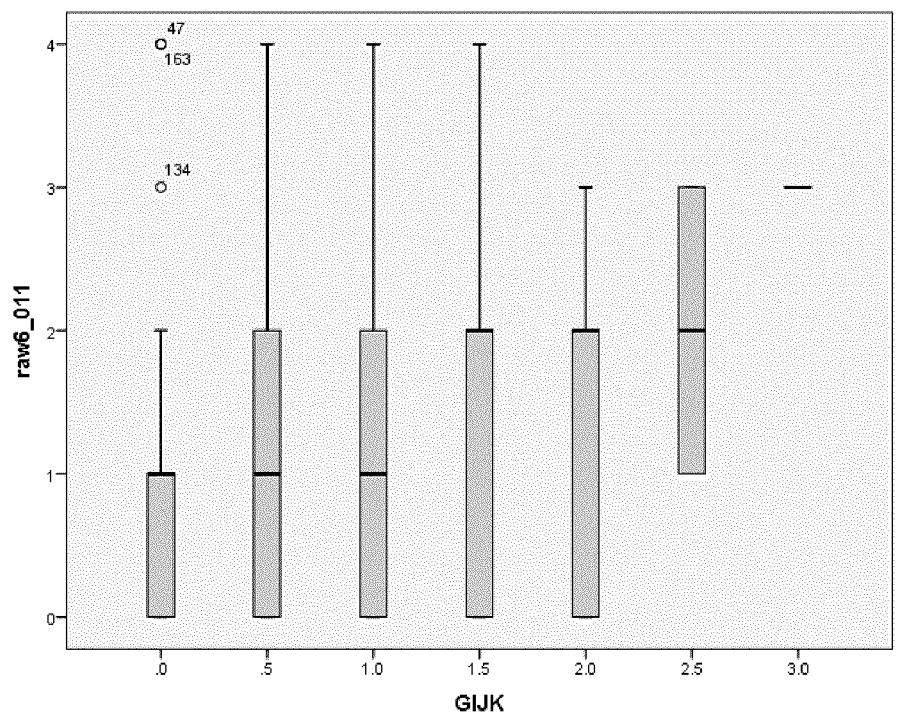
FIG. 24: Boxplot showing raw suicide severity scores (y-axis) across the additive genotype risk scores (x-axis) for markers GIJK (as identified in Table 8).
Figure 25:
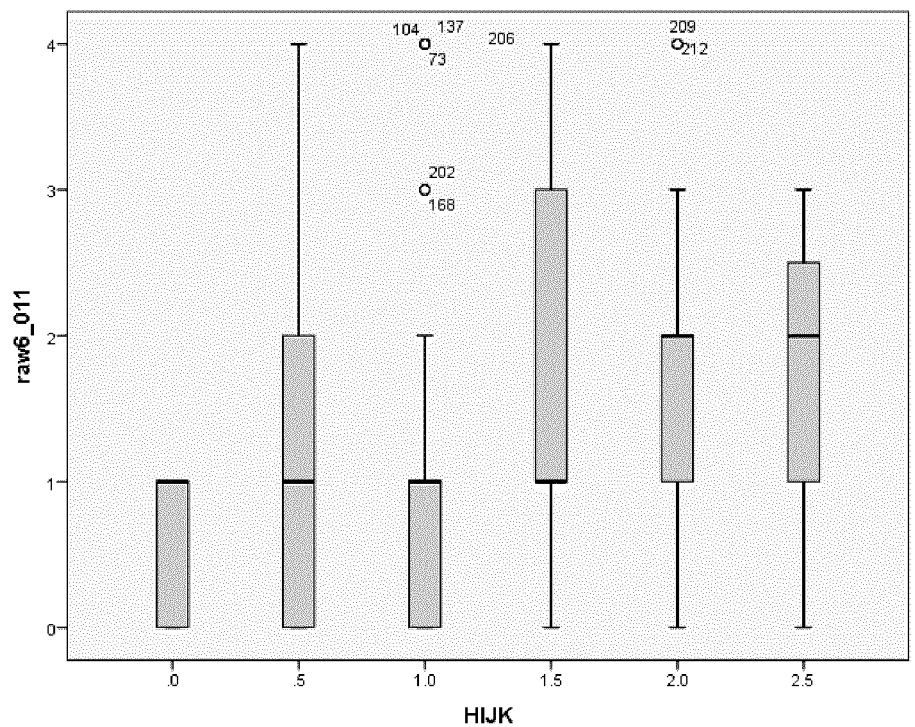
FIG. 25: Boxplot showing raw suicide severity scores (y-axis) across the additive genotypic risk scores (x-axis) for markers HIJK (as identified in Table 8).
Figure 26:
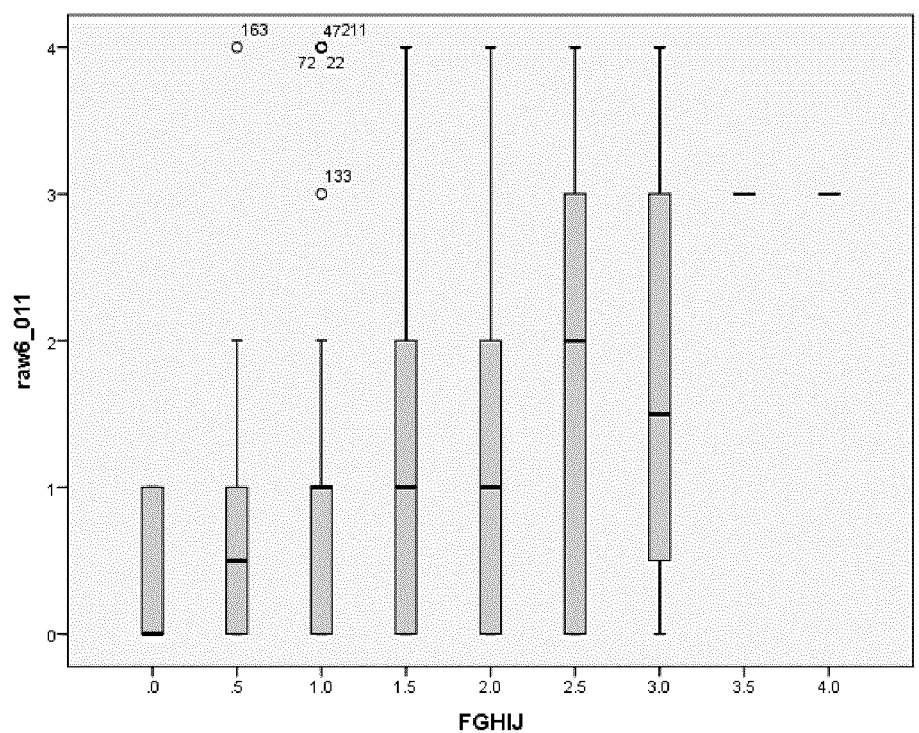
FIG. 26: Boxplot showing raw suicide severity scores (y-axis) across the additive genotypic risk scores (x-axis) for markers FGHIJ (as identified in Table 8).
Figure 27:
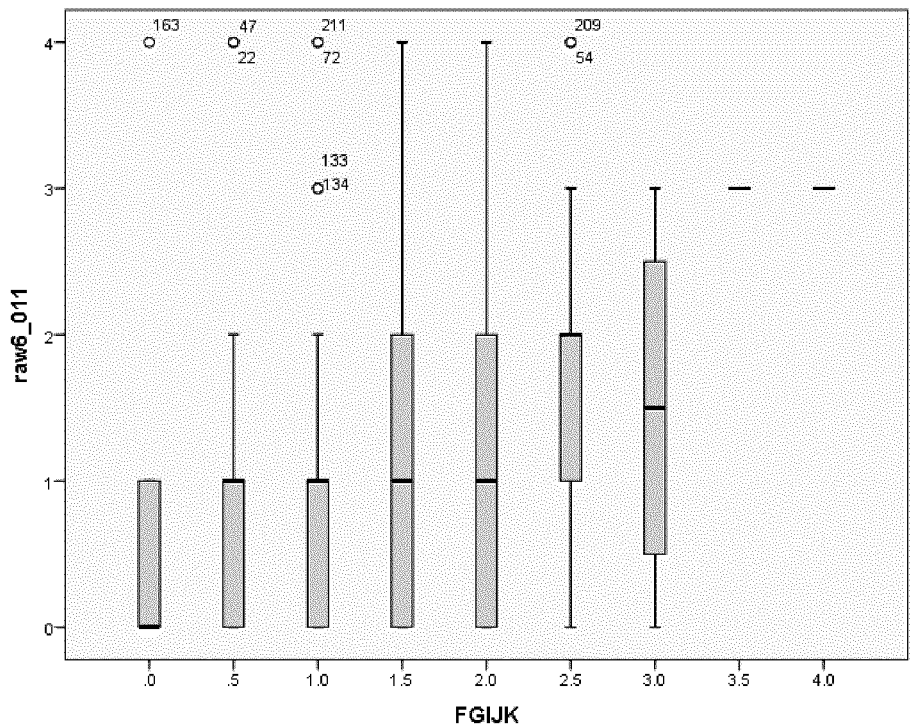
FIG. 27: Boxplot showing raw suicide severity scores (y-axis) across the additive genotypic risk scores (x-axis) for markers FGIJK (as identified in Table 8).
Figure 28:
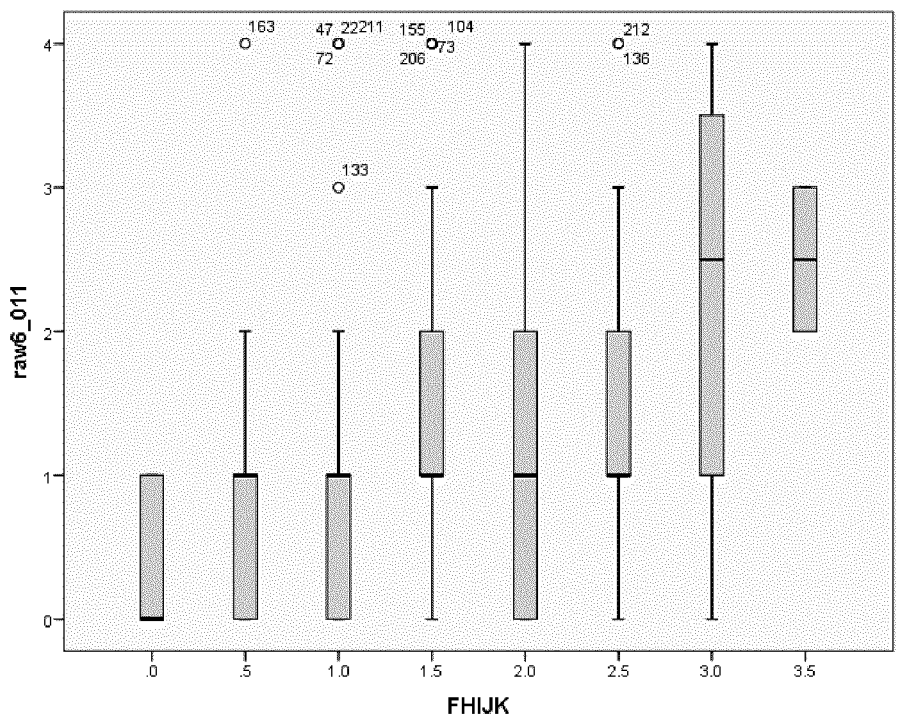
FIG. 28: Boxplot showing raw suicide severity scores (y-axis) across the additive genotype risk scores (x-axis) for markers FHIJK.

The present subject matter relates in part to the discovery of certain genetic markers that are informative regarding a subject's risk of severe suicidal behavior (SSB). In this context, SSB includes one or more of suicide attempt and active suicidal thoughts. The markers were discovered by the present inventors in what is believed to be the first GWAS of suicidal behavior severity in bipolar disorder (BD) patients and in a GWAS of suicide attempt in BD patients. The genetic markers are in the form of single nucleotide polymorphisms (SNPs) determined by the inventors to be informative regarding risk of SSB. For example, the inventors found that panels of particular markers could account for at least 5% of the variance in risk for SSB. In addition, the impact of certain combinations of markers was found to be even greater, accounting for up to from about 6% to about 10%, or from about 8% to about 10% of the variance in risk for SSB.

The methods of the invention provide an output containing actionable information regarding a subject's risk of SSB based in part upon the subject's genotype al one or more SNPs, as described herein, and optionally one or more additional subject specific factors as described below. The methods described here were developed using data obtained from subjects who had been diagnosed with bipolar depression but the methods are generalizable to persons who have been diagnosed with depression, including major depressive disorder, as well as subjects who have not been diagnosed with any psychiatric disorder. The methods are useful, for example, in screening subjects to identify individuals who are at a higher risk for SSB than the general population. Such methods are useful, for example, in identifying at-risk individuals for early interventions aimed at providing appropriate treatments in the form of medication or therapy, or both, and thereby reducing that risk for the individual. The present methods are also useful tools in screening subjects, e.g., for participation in clinical trials, especially clinical trials involving a drug being developed for a psychiatric indication, to treat epilepsy, and other neurologic drugs with central nervous system (CNS) activity. The present methods may also be useful tools in screening subjects who will be engaging in high stress activities that may potentiate SSB, including, e.g., military service, police service, piloting a commercial airline, firefighting, etc.

In one embodiment, the subject is a psychiatric patient. As used herein, the term "psychiatric patient" refers to a human subject having a diagnosis indicating that the subject is in need of therapy or treatment with one or more medications and/or therapies to alleviate one or more symptoms of a psychiatric disease or disorder. In one embodiment, the one or more medications is an antipsychotic or antidepressant medication.

The output of risk provided by the methods of the invention is referred to herein as the "severe suicidal behavior risk assessment" or "SSB risk assessment". This risk assessment incorporates information about the subject's genotype at one or more of SNPs identified herein, or one or more panels of SNPs as defined herein. In addition, the risk assessment may optionally incorporate one or more additional data attributes (also interchangeably referred to as features or factors), including for example, the subject's diagnosis, concomitant medications, comorbidities, age, gender, ethnicity, childhood trauma, stressful life events, alcohol use, use of controlled substances, and use of psychotropic agents.

In one embodiment, the invention provides a method for determining a subject's risk of SSB, the method comprising determining or receiving the subject's genotype for one or more of the SNPs listed in Table 1, or one or more of the panels of SNPs listed in Table 2. In one embodiment, the method comprises determining or receiving the subject's genotype for at least 2, at least 3, at least 4, at least 5, or all 6 of the SNPs (F-K) in Table 1 or at least one of the panels (1-22) of SNPs listed in Table 2.

In one embodiment, the methods of the invention further comprise an output indicating a suggested intervention based upon the subject's risk assessment as determined by the methods of the present invention. For example, for individuals identified as being at low risk for SSB, intervention as usual with monitoring on a regular basis would be suggested. For individuals identified as being at intermediate risk for SSB, interventions may include more frequent visits and monitoring, medication adjustments, augmentation with other therapies, including and not limited to psychotherapies, cognitive behavioral therapy, and brain stimulation. For individuals identified as being at high risk for SSB, in addition to interventions considered for individuals at intermediate risk, considering hospitalization that might include higher levels of observations of these individuals. Treating physicians may advise family members and alert other caregivers (for example, community nurses, social workers, and mental health workers) to increase vigilance.

Current methods for assessing suicidal ideation and behavior rely primarily upon actively querying patients about the occurrence of suicidal thinking and behavior, or relying on patients to report such occurrences spontaneously, followed by retrospective classification of the events into appropriate categories. Generally acceptable categories and definitions include, for example, those outlined by Posner et al. in the Columbia-Suicide Severity Rating Scale (C-SSRS) and those outlined in Section 6 (e.g., Section 6.011) of the Schedules for Clinical Assessment in Neuropsychiatry (SCAN), a set of tools created by the World Health Organization aimed at diagnosing and measuring mental illness (see Wing J K, et al. SCAN: Schedules for Clinical Assessment in Neuropsychiatry. *Arch Gen Psychiatry.* 1990; 47(6):589-593). Typically, one goal of the questionnaire is to identify individuals who have contemplated suicide (suicidal ideation) and assess the severity of their suicidal ideation as an indicator of the subject's risk for severe suicidal behavior. For example, the questionnaire may seek to determine whether the subject entertains a passive wish to be dead or has other, non-specific active suicidal thoughts (without any method, intent, or plan). Such a passive wish or non-specific but active suicidal thoughts would be rated low on a sliding scale of suicidal behavior severity. Active suicidal thoughts, including one or more of a planned method, manner of carrying it out, and intent to do so, would be rated high on a scale of suicidal behavior severity. In addition, the questionnaire seeks to categorize the severity of any reported suicidal behavior such as self-injurious behavior without suicidal intent, preparatory acts toward imminent suicidal behaviors, aborted suicide attempt, interrupted suicide attempt, and suicide attempt.

In the context of the present invention, the subject is a human subject, in certain embodiments, the human subject is selected from an adult subject, an adult male subject, a pediatric subject, or an elderly (geriatric) subject, as those terms are understood in the medical arts. In certain embodiments, the subject is further defined according to the subject's ethnicity. For example, in one embodiment the subject self-identifies or is genetically determined to be a member of an ethnic group selected from African, North African, Southern African, European, Western European, Northern European, Asian, Japanese, Han Chinese, and Korean. In one embodiment, the subject is of European ethnicity. In this context, the terms ethnicity and ancestry are used interchangeably.

In one embodiment, the methods of the invention are directed to subjects who have been diagnosed with a psychiatric disorder. In one embodiment, the psychiatric disorder is a depressive disorder. In one embodiment, the subject has been diagnosed with major depressive disorder (also referred to as clinical depression, or recurrent depression). In one embodiment, the psychiatric disorder is bipolar disorder. In one embodiment, the subject presents with one or more symptoms selected from the group consisting of catatonia, depressed mood, severe obsessions and/or compulsions or psychomotor agitation. In one embodiment, the subject presents with one or more symptoms of mania, including but not limited to elevated, expansive or irritable mood, exaggerated goal-directed activity, inflated self-esteem or grandiosity and decreased need for sleep. In one embodiment, the subject presents with one or more symptoms of impulse-control, conduct or disruptive disorders including failure to control aggressive impulses, aggression to people/animals/property and serious violations of widely accepted rules.

In another embodiment, the methods of the invention are directed to subjects who have not been diagnosed with any psychiatric disorder.

In one embodiment, the methods of the invention, in addition to outputting the SSB risk assessment, further comprise outputting a recommended course of action or therapy. The recommended course of action or therapy may include one or more of, a specific medication for administering to the patient, patient monitoring, including an increase or decrease in current monitoring of the patient, and counseling, including but not limited to cognitive behavioral therapy. In one embodiment, the medication is selected from a selective serotonin reuptake inhibitor (SSRI) and an irreversible monoamine oxidase inhibitor (MOI). In one embodiment, the medication is selected from an SSRI, an MOI, eicosapentaenoic acid (EPA), a COX-2 inhibitor, and lithium.

Genetic Markers and Combinations

In one embodiment, the methods of the invention comprise determining or receiving a subject's genotype at one or more SNPs selected from the SNPs listed in Table 1 (markers F through K), or at least one panel of SNPs selected from the panels listed in Table 2.

In one embodiment, the methods of the invention comprise determining or receiving a subject's genotype for at least two SNPs selected from the SNPs listed in Table 1 (markers F through K). In one embodiment, the at least two SNPs comprises markers F and H (as identified in Table 8). In one embodiment, the methods of the invention comprise determining or receiving a subject's genotype for at least three SNPs selected from the SNPs listed in Table 1 (markers F through K). In one embodiment, the at least three SNPs comprises markers F, H, and either I or K, or both (as identified in Table 8).

In one embodiment, the methods of the invention comprise determining or receiving a subject's genotype for one or more panels of SNPs selected from the panels listed in Table 2. In one embodiment, the one or more panels is selected from a panel that accounts for at least 5% of the variance in risk for SSB, e.g., a panel selected from panels 1, 3-17, and 19-22 in Table 2. In one embodiment, the one or more panels is selected from a panel that accounts for at least 6% of the variance in risk for SSB, e.g., a panel selected from panels 1, 3-5, 7-11, 13-17, and 19-22 in Table 2. In one embodiment, the one or more panels is selected from a panel that accounts for at least 7% of the variance in risk for SSB, e.g., a panel selected from panels 1, 3-5, 9-11, 13, 14, 16, and 19-22 in Table 2. In one embodiment, the one or more panels is selected from a panel that accounts for at least 8% of the variance in risk for SSB, e.g., a panel selected from panels 3-5, 9-11, 13, 14, 20 and 22 in Table 2. In one embodiment, the one or more panels is selected from a panel that accounts for al least 9% of the variance in risk for SSB, e.g., a panel selected from panels 9, 13, 20 and 22 in Table 2.

In general individuals with genotype risk scores of greater than 1.5 were classified as at intermediate or high risk for SSB and those having risk scores of at least 1.5, at least 2.0, or al least 3.0 were generally classified as high risk for SSB. In general individuals with genotype risk scores of 1.5 or less were generally classified as being at low risk for SSB. The specific risk classifications associated with each panel of markers is shown in Table 2.

In one embodiment of any of the foregoing methods, the method further comprises determining or receiving the subject's genotype at one or more additional SNPs selected from those listed in Table 3 (markers A through E).

Throughout this disclosure, SNPs are referred to by their "rs" number as well as a reference sequence (sec Tables 1 and 3 for SNP reference sequences and their sequence identifiers as used herein). The reference sequence shows the single nucleotide polymorphism in bold. The "rs" number for a given SNP is a reference number provided by the HapMap consortium. The rs number is sufficient to obtain much of the known information regarding a particular SNP, for example by querying the rs number in the HapMap database or similar databases including the UCSC Genome Bioinformatics Web Page and similar databases maintained by the US National Center for Biotechnology Information.

In one embodiment the risk assessment is qualitative, e.g., high, intermediate, low. In another embodiment, the risk assessment is a numerical value. The risk assessment incorporates the subject's total genetic risk score for one or more SNP's included in the method. The total genetic risk score is the sum of the individual risk scores for each genotype of each SNPs included, e.g., in a panel of SNPs as defined infra. The genotypes are coded as "1" for homozygotes for risk allele (high-risk genotype), "0.5" for heterozygotes (intermediate-risk genotype), and "0" for homozygotes for the protective allele (low-risk genotype). Tables 1 and 2 list the genotypes and risk scores for each genotype of each SNP described herein. Table 2 lists the genotypes and risk scores for panels of SNPs described herein.

In one embodiment, the methods may incorporate other relevant information into the risk assessment. For example, the methods may incorporate information regarding the subject's ethnicity, age, and gender. In one embodiment, the risk assessment incorporates information regarding the subject's ethnicity. The methods may also incorporate other factors, including patient specific environmental factors such as childhood trauma, stressful life events, alcohol use, use of controlled substances, and use of psychotropic agents; and the subject's diagnosis, concomitant medications, comorbidities, age, gender, and ethnicity.

As discussed in the following sections, the risk assessment is used in methods to improve therapeutic outcomes by preventing or reducing the risk of SSB in a subject; for selecting an appropriate therapy or intervention to reduce the risk of SSB; and for screening to identify at-risk individuals. The risk assessment is also useful in methods for designing a therapeutic regimen for a patient that minimizes the patient's risk of SSB.

The methods may also include generating and outputting a patient-specific report identifying the patient according to the patient's risk, providing an assessment of that risk, and including proposed therapies and/or interventions tailored to the patient's risk.

TABLE 1

SNPs associated with SSB and associated genotype risk scores.
Sequences are shown as on the positive chromosomal strand.

| Ref. | SNP | Genotype Risk Scores | Ref. Seq | Sequence |
|---|---|---|---|---|
| F | rs2610025 | CC 1/CA 0.5/AA 0 | SEQ ID NO: 1 | ACTCATTTGGCTTAAAATTTTATTT[C/A]CTAATTTTGCAGAATGACCCTTAGG |
| G | rs10448044 | CC 1/CT 0.5/TT 0 | SEQ ID NO: 2 | CAGCCACCGCTGGACAAAGAATGGA[C/T]GTGGCCACAGGAACTGCTGCCACTA |
| H | rs7079041 | AA 1/AG 0.5/GG 0 | SEQ ID NO: 3 | AGAACAGTGGATATTGGTGATCAGC[A/G]AATGTTGCTGCCTGATCGTTCCTCT |
| I | rs720903 | AA 1/AT 0.5/TT 0 | SEQ ID NO: 4 | ACCCTTGCCTCCCAAAGTGTTGAGA[A/T]TATGAGCGTGAGCCACCATGCCCAG |

TABLE 1-continued

SNPs associated with SSB and associated genotype risk scores.
Sequences are shown as on the positive chromosomal strand.

| Ref. | SNP | Genotype Risk Scores | Ref. Seq | Sequence |
|---|---|---|---|---|
| J | rs10483836 | GG 1/GT 0.5/TT 0 | SEQ ID NO: 5 | TATAATTTGATCCTTTAGTTGTATT[G/T]TGATGATCACTTGGAATAACATTCA |
| K | rs7244261 | TT 1/CT 0.5/CC 0 | SEQ ID NO: 6 | TAAAATAACTCAGGTATTTTAAAAT[C/T]CAAAATAAAATATAATCTCTCAATT |

TABLE 2

Panels of SNPs associated with SSB and associated genotype risk scores (additive genotype risk scores from the indicated combinations of markers)

| Panel # | SNPs (human) | Genotype risk score | # Individuals (% of total) | Suicide Severity Group | % Variance in SSB risk explained |
|---|---|---|---|---|---|
| 1 | F, H | 0 | 23 (0.097) | Low | 7.6 |
| | | 0.5 | 79 (0.333) | Intermediate | |
| | | 1.0 | 80 (0.338) | Intermediate | |
| | | 1.5 | 47 (0.198) | Intermediate | |
| | | 2.0 | 8 (0.034) | High | |
| 2 | G, H | 0 | 61 (0.257) | Intermediate | 5 |
| | | 0.5 | 98 (0.414) | Intermediate | |
| | | 1.0 | 59 (0.249) | Intermediate | |
| | | 1.5 | 19 (0.080) | High | |
| 3 | F, G, H | 0 | 17 (0.072) | Low | 8 |
| | | 0.5 | 54 (0.228) | Intermediate | |
| | | 1.0 | 74 (0.312) | Intermediate | |
| | | 1.5 | 57 (0.241) | Intermediate | |
| | | 2.0 | 29 (0.122) | High | |
| | | 2.5 | 6 (0.025) | High | |
| 4 | F, H, I | 0 | 19 (0.080) | Low | 9 |
| | | 0.5 | 67 (0.283) | Intermediate | |
| | | 1.0 | 83 (0.350) | Intermediate | |
| | | 1.5 | 51 (0.215) | Intermediate | |
| | | 2.0 | 16 (0.068) | High | |
| | | 2.5 | 1 (0.004) | High | |
| 5 | F, H, K | 0 | 18 (0.076) | Intermediate | 8.6 |
| | | 0.5 | 57 (0.241) | Intermediate | |
| | | 1.0 | 74 (0.312) | Intermediate | |
| | | 1.5 | 60 (0.253) | Intermediate | |
| | | 2.0 | 19 (0.080) | High | |
| | | 2.5 | 8 (0.034) | High | |
| | | 3.0 | 1 (0.004) | High | |
| 6 | G, H, J | 0 | 33 (0.139) | Intermediate | 5.6 |
| | | 0.5 | 86 (0.363) | Intermediate | |
| | | 1.0 | 65 (0.274) | Intermediate | |
| | | 1.5 | 42 (0.177) | Intermediate | |
| | | 2.0 | 10 (0.042) | High | |
| | | 2.5 | 1 (0.004) | High | |
| 7 | G, H, K | 0 | 43 (0.181) | Intermediate | 6.4 |
| | | 0.5 | 79 (0.333) | Intermediate | |
| | | 1.0 | 71 (0.300) | Intermediate | |
| | | 1.5 | 31 (0.131) | High | |
| | | 2.0 | 11 (0.046) | High | |
| | | 2.5 | 2 (0.008) | High | |
| 8 | H, J, K | 0 | 44 (0.186) | Intermediate | 6.1 |
| | | 0.5 | 73 (0.308) | Intermediate | |
| | | 1.0 | 69 (0.291) | Intermediate | |
| | | 1.5 | 40 (0.169) | High | |
| | | 2.0 | 11 (0.046) | High | |
| 9 | F, G, H, I | 0 | 15 | Low | 9.2 |
| | | 0.5 | 42 | Intermediate | |
| | | 1.0 | 77 | Intermediate | |
| | | 1.5 | 60 | Intermediate | |
| | | 2.0 | 32 | High | |
| | | 2.5 | 8 | High | |
| | | 3.0 | 3 | High | |
| 10 | F, G, H, J | 0 | 11 | Low | 8.4 |
| | | 0.5 | 37 | Intermediate | |
| | | 1.0 | 61 | Intermediate | |
| | | 1.5 | 66 | Intermediate | |
| | | 2.0 | 38 | Intermediate | |
| | | 2.5 | 21 | High | |
| | | 3.0 | 2 | High | |
| | | 3.5 | 1 | High | |
| 11 | F, G, H, K | 0 | 13 | Intermediate | 8.8 |
| | | 0.5 | 42 | Intermediate | |
| | | 1.0 | 64 | Intermediate | |
| | | 1.5 | 60 | Intermediate | |
| | | 2.0 | 31 | High | |
| | | 2.5 | 23 | High | |
| | | 3.0 | 3 | High | |
| | | 3.5 | 1 | High | |
| 12 | F, G, J, K | 0 | 20 | Intermediate | 6 |
| | | 0.5 | 50 | Intermediate | |
| | | 1.0 | 54 | Intermediate | |
| | | 1.5 | 66 | Intermediate | |
| | | 2.0 | 34 | High | |
| | | 2.5 | 9 | High | |
| | | 3.0 | 3 | High | |
| | | 3.5 | 1 | High | |
| 13 | F, H, I, J | 0 | 14 | Low | 9.1 |
| | | 0.5 | 42 | Intermediate | |
| | | 1.0 | 70 | Intermediate | |
| | | 1.5 | 71 | Intermediate | |
| | | 2.0 | 27 | Intermediate | |
| | | 2.5 | 12 | High | |
| | | 3.0 | 1 | High | |
| 14 | F, H, J, K | 0 | 13 | Intermediate | 8.8 |
| | | 0.5 | 42 | Intermediate | |
| | | 1.0 | 57 | Intermediate | |
| | | 1.5 | 60 | Intermediate | |
| | | 2.0 | 44 | High | |
| | | 2.5 | 17 | High | |
| | | 3.0 | 4 | High | |
| 15 | G, H, I, J | 0 | 26 | Intermediate | 6.9 |
| | | 0.5 | 77 | Intermediate | |
| | | 1.0 | 71 | Intermediate | |
| | | 1.5 | 45 | Intermediate | |
| | | 2.0 | 15 | High | |
| | | 2.5 | 2 | High | |
| | | 3.0 | 1 | High | |
| 16 | G, H, I, K | 0 | 34 | Intermediate | 7.6 |
| | | 0.5 | 73 | Intermediate | |
| | | 1.0 | 75 | Intermediate | |
| | | 1.5 | 39 | Intermediate | |
| | | 2.0 | 11 | High | |
| | | 2.5 | 3 | High | |
| | | 3.0 | 2 | High | |
| 17 | G, H, J, K | 0 | 28 | Intermediate | 7 |
| | | 0.5 | 60 | Intermediate | |
| | | 1.0 | 64 | Intermediate | |
| | | 1.5 | 54 | Intermediate | |

TABLE 2-continued

Panels of SNPs associated with SSB and associated genotype risk scores (additive genotype risk scores from the indicated combinations of markers)

| Panel # | SNPs (human) | Genotype risk score | # Individuals (% of total) | Suicide Severity Group | % Variance in SSB risk explained |
|---|---|---|---|---|---|
| | | 2.0 | 24 | High | |
| | | 2.5 | 6 | High | |
| | | 3.0 | 1 | High | |
| 18 | G, I, J, K | 0 | 52 | Intermediate | 4.6 |
| | | 0.5 | 64 | Intermediate | |
| | | 1.0 | 84 | Intermediate | |
| | | 1.5 | 25 | High | |
| | | 2.0 | 9 | High | |
| | | 2.5 | 2 | High | |
| | | 3.0 | 1 | High | |
| 19 | H, I, J, K | 0 | 35 | Intermediate | 7.5 |
| | | 0.5 | 67 | Intermediate | |
| | | 1.0 | 75 | Intermediate | |
| | | 1.5 | 42 | Intermediate | |
| | | 2.0 | 15 | High | |
| | | 2.5 | 3 | High | |
| 20 | F, G, H, I, J | 0 | 10 | Low | 9.7 |
| | | 0.5 | 30 | Intermediate | |
| | | 1.0 | 55 | Intermediate | |
| | | 1.5 | 71 | Intermediate | |
| | | 2.0 | 41 | Intermediate | |
| | | 2.5 | 24 | High | |
| | | 3.0 | 4 | High | |
| | | 3.5 | 1 | High | |
| | | 4.0 | 1 | High | |
| 21 | F, G, I, J, K | 0 | 17 | Low | 7.1 |
| | | 0.5 | 46 | Intermediate | |
| | | 1.0 | 44 | Intermediate | |
| | | 1.5 | 77 | Intermediate | |
| | | 2.0 | 34 | Intermediate | |
| | | 2.5 | 13 | High | |
| | | 3.0 | 4 | High | |
| | | 3.5 | 1 | High | |
| | | 4.0 | 1 | High | |
| 22 | F, H, I, J, K | 0 | 11 | Low | 10.2 |
| | | 0.5 | 34 | Intermediate | |
| | | 1.0 | 57 | Intermediate | |
| | | 1.5 | 61 | Intermediate | |
| | | 2.0 | 45 | Intermediate | |
| | | 2.5 | 23 | Intermediate | |
| | | 3.0 | 4 | High | |
| | | 3.5 | 2 | High | |

(3) transmitting, advising and/or conveying the results of the risk assessment to a physician, medical service provider or other third party, and (4) altering the subject's treatment regimen based on the results of the risk assessment in order to lower the subject's risk. These range from medication adjustments, cognitive behavioral therapy, brain stimulation, increased monitoring, and hospitalization.

The genotype of the subject is determined by techniques known in the art, for example, PCR analysis, DNA sequencing, 5'exonuclease fluorescence assay, sequencing by probe hybridization, dot blotting, oligonucleotide array (DNA chip) hybridization analysis, and "Next-generation sequencing" methods, referring to non-Sanger-based high-throughput DNA sequencing technologies, or combinations thereof. Next generation sequencing systems and services are commercially available, for example through companies such as Life Technologies, Inc. and Illumina, Inc. Real-time PCR methods that can be used to detect SNPs, include, e.g., Taqman or molecular beacon-based assays (U.S. Pat. Nos. 5,210,015; 5,487,972; and PCT WO 95/13399) are useful to monitor for the presence or absence of a SNP. Genotyping technology is commercially available, for example from companies such as Applied Biosystems, Inc (Foster City, Calif.).

Any suitable biological sample from the subject can be used as the source of the DNA for genotyping. In one embodiment, the biological sample is a sample of saliva. In another embodiment, the biological sample is a blood sample.

Kits

The present invention also diagnostic products and kits for practicing the methods of the present invention. In one embodiment, a kit provided by the invention comprises a set of primers adapted to amplify, in a polymerase chain reaction, at least one nucleotide sequence comprising a single nucleotide polymorphism (SNP) as defined by the SNPs identified in Table 1. In another embodiment, the kit comprises at least two or more sets of primers adapted to amplify a panel of SNPs selected from the panels identified in Table 2.

In one embodiment, a kit provided by the invention comprises one or more nucleic acid probes adapted to identify the presence of at least one SNP identified in Table 1, or at least one panel of SNPs identified in fable 2. In one

TABLE 3

SNPs associated with SSB and associated genotype risk scores.
Sequences are shown as on the positive chromosomal strand.

| Ref. | SNP | Genotype Risk Scores | Ref. Seq | Sequence |
|---|---|---|---|---|
| A | rs2491144 | GG 1/GA 0.5/AA 0 | SEQ ID NO: 7 | CAAGTTCCTTCTGTCTTGTTAAGCT[A/G]TTGTCATTCCGTGTTGCCCTCATTC |
| B | rs9315639 | CC 1/CT 0.5/TT 0 | SEQ ID NO: 8 | CATGCTACAGTCACCTAAAACCTGT[C/T]CTGGCTTGGATAGAATATCTTCCCA |
| C | rs11082138 | CC 1/CT 0.5/TT 0 | SEQ ID NO: 9 | GTATTTGTATTCAATCTCCACTTCA[C/T]TGGAAACTTCTTGAGGACAAATGTG |
| D | rs11697517 | TT 1/CT 0.5/CC 0 | SEQ ID NO: 10 | ATACTAAATGTTAACTTCTGCAAGT[C/T]CCTTTTCTCACTCAACATTACTGTA |
| E | rs2186437 | CC 1/CA 0.5/AA 0 | SEQ ID NO: 11 | CAGGCTGGAATCTAGTGGTGTCAAC[A/C]TATCTCCTTTTAGCCTTGAACTCCT |

In one embodiment, the methods of the invention further comprise one or more additional steps selected from the group consisting of (1) testing the subject for one or more additional genetic markers, (2) advising and/or counseling the subject with respect to the results of the risk assessment, embodiment, the probe comprises at least one, two, or three or more nucleotides on each side of the polymorphic site.

The nucleic acid primers and probes may be of any suitable length for use in amplifying or detecting the SNPs described herein and the optimal length may be readily determined using techniques known to the skilled person. In one embodiment, the probe is labeled with a detectable marker, for example, a marker that emits light or radioactivity, or is otherwise identifiable or selectable, e.g., via binding to a substrate or target molecule. Means for labeling nucleic acid probes and for detecting such labels are known in the art.

The kits of the present invention may also optionally comprise one or more reagents and/or products including, but not limited to, one or more buffers for performing PCR or probe hybridization, or any step in such a process as would be known to a person of skill in the art, one or more DNA amplifying enzymes, or any combination thereof; one or more reagents, components and products for genotyping the polymorphisms as described herein, including, but not limited to those used in exonuclease assays, nucleotide sequencing, or any combination thereof; one or more reagents, components or products for performing a DNA sequencing reaction that determines the sequence of a nucleotide sequence of an SNP defined herein; a gene chip or array comprising one or a plurality of nucleotide sequences comprising or consisting of those identified in any one of Tables 1, 2, and 3.

System

Figure 29:
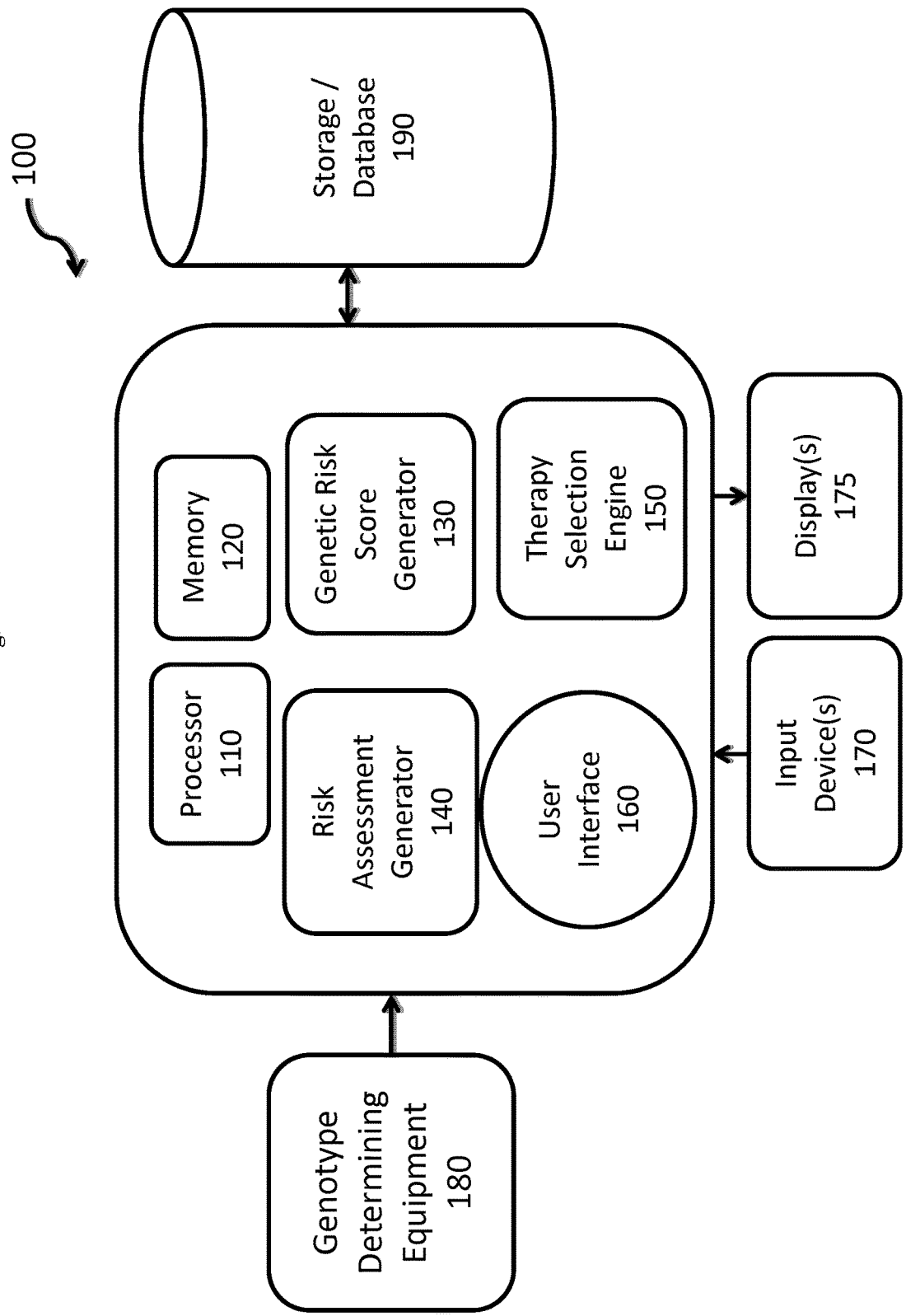
FIG. 29: Schematic of a computer system for implementing one or more features of the invention.

FIG. 29 illustrates an example of a system that can implement one or more features described herein. Here, system 100 includes a processor 110 and a memory 120. In some embodiments, memory 120 can include executable instructions that when executed by processor 110, cause the processor 110 to perform one or more operations discussed herein. System 100 also includes a user interface 160 which permits the system to interact with a user through, for example, one or more input devices 170 and one or more displays 175.

System 100 can also include one or more modules and/or engines that implement one or more features described herein. For example, system 100 can include Genetic Risk Score Generator 130, which can, for example, generate a total genetic risk score for a subject. System 100 can also include a Risk Assessment Generator 140 which can, for example, generate a risk assessment for the subject using one or more data attributes including the subject's total genetic risk score. Moreover, system 110 can include a Therapy Selection Engine 150, which can, for example, select an appropriate therapy or intervention for the subject based on the subject's risk assessment.

In some embodiments, system 100 can be configured to receive a patient's data from genotype determining equipment 180. In some embodiments, one or more patient data can be stored in a data storage or database 190 which is connected to the system via a data connection.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, modules, model generators, computer instructions, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

EXAMPLES

The present invention is further illustrated by the following examples.

Example 1

A GWAS of suicide behaviour severity was conducted in a sample of 428 BD cases from Toronto. Imputation with 1000 Genome Project data was carried out as reference using IMPUTE2. Quality control and data analysis was conducted using PLINK and R. The quantitative analysis of suicide behaviour severity was conducted. Data was collected via a GWAS using the quantitative variable of suicide severity in BD patients. As discussed below, we identified two chromosomal regions of interest in this GWAS of suicide in BD patients.

Methods

The characteristics of the sample included in this study have been described previously (Scott et al, 2009; Xu et al, 2014). The sample consisting of 428 BD patients (Sample CA2) was recruited at CAMH, Details on the CA2 sample have been described previously (Scott et al, 2009). The participants were at least 18 years of age at time of enrolment and European ancestry by self-report. They were recruited through advertisements in family doctors' offices, clinics, hospitals, and patient support groups. Their diagnoses for BD according to DSM-IV and ICD-10 criteria were confirmed using the Schedules for Clinical Assessment in Neuropsychiatry (SCAN). Exclusion criteria included a diagnosed or reported dependence on intravenous drugs, the presence of mood incongruent psychotic features, and the presence of manic episodes that are only concurrent with or as a result of alcohol, substance abuse or dependence, medication, or medical conditions. Their suicidality was assessed using the Suicide Severity item within the Schedules for Clinical Assessment in Neuropsychiatry (SCAN) as follows: 0 for non-suicidal, 1 for deliberately considering suicide or self-harm, 2 for injuring self or making an attempt without serious consequences; 3 for serious self-harm or attempt; 4 for an attempt at suicide designed to be lethal. More details on sample characteristics are shown in Table 4. All procedures contributing to this work abide by the Declaration of Helsinki in 1975 (revised in 2008), and the ethical standards of the national and institutional committees on human experimentation.

TABLE 4

Demographic information on the bipolar disorder sample included in the genome-wide association study of suicide behaviour severity.

| Bipolar_Disorder_Sample | CA2 |
|---|---|
| Site | CAMH |
| Number_of_Cases | 308 |
| Genotyping_platform | Illumina Sentrix Human Hap550 Beadchip |
| Suicide_Measure | SCAN 6.011 |
| Number_of_SNPs_before_imputation | 438625 |
| Average_Age (Std_Dev) | 43.06 +/− 12.41 |
| Sex_Ratio (% Male) | 0.4 |

Sample CA2 was genotyped with the IlluminaSentrix Human Hap550 Beadchip (Illumina Inc., San Diego, Calif., USA) mostly at Illumina Inc. (San Diego, Calif., USA), with 290 subjects from the CA2 sample being genotyped at the Genome Quebec facility (Montreal, Quebec, Canada).

Quality control measures were applied for the CA2 sample separately using PLINK (Purcell et al, 2007) and R (R Development Core Team (2008). R: A language and environment for statistical computing. R Foundation for Statistical Computing, Vienna, Austria. ISBN 3-900051-07-0, URL http://www.R-project.org.). Briefly, individuals with less than 95% of the markers genotyped were removed, and markers that were less than 95% genotyped or had a minor allele frequency of less than 5% were excluded. Cryptic relatedness was assessed and one individual of each pair of related individuals (defined as pairs with PI_HAT>0.05) was removed if there is more missing phenotype or genotype information for that individual. Sex was matched with genetic data. Mean heterozygosity was determined, and outliers were removed. Markers of which genotypes deviated significantly from Hardy-Weinberg Equilibrium (p<0.0001) were excluded from subsequent analyses. A multi-dimensional scaling (MDS) analysis of the genotypes was run to ascertain the ethnicity of the samples, and the discrete cluster that corresponded to the self-reported Jewish ancestry for all four grandparents was removed. After sample refinement and updating map position to build 37, 438,625 markers remained for 308 CA2 cases.

A whole-genome imputation using IMPUTE2 (Howie et al, 2012) was conducted in 5-Mb segments alter prephasing in SHAPEIT2 (Delaneau et al, 2013) for the CA2 sample using the 1000 Genome Project (Genomes Project et al, 2010) build 37 macGT1 (Haplotype release date: March 2012) data as reference. The output to PLINK format was then converted using GTOOL (Genetics Software Suite, © 2007, The University of Oxford) with an imputation score threshold of 0.9. Afterwards, quantitative analyses on the suicide severity variables was performed (linear regression on suicide severity for both CA2) in PLINK. Age, sex, past alcohol dependence/abuse, the number of depressive episodes, and the first two components from the multidimensional scaling (MDS) analysis were included as covariates. To compare these findings with those of previous suicide GWAS (Willour et al, 2012), analyses on suicide attempt history (logistic regression for CA2—with patients scoring 2 or above on the SCAN Suicide Severity item) was also performed in PLINK. Thus these suicide attempters included patients who have had non-suicidal self-injury.

Results

Genotypes for 2,659,407 markers were obtained after imputation with the 1000 Genome Project data.

Markers in two chromosomal regions were found to be associated with suicide severity (Table 5: 14 markers with uncorrected p<0.05). The first region of interest resides within chromosome 8q12, close to the long intergenic non-protein coding RNA gene LINC00968 and the proenkephalin gene PENK. The second stretch is located at chromosomal location 10p11.2, which encompasses the genes CCDC7 (coiled-coil domain containing 7), C10orf68 (chromosome 10 open reading frame 68), and ITGB1 (integrin, beta 1 (fibronectin receptor, beta polypeptide, antigen CD29 includes MDF2, MSK12)). The minor allele frequencies of the top markers in this study mirrored those of the European sample from the 1000 Genome Project.

In addition to GWAS of suicide severity, a GWAS of suicide attempt in the CA2 sample was also performed (Table 6: four markers with uncorrected p<0.05). Two regions of suggestive associations were found. The first was localized to 8q12-q21 and was approximately 400 kb upstream of the interleukin 7 (IL7) gene. The second was approximately 150 kb downstream of the thioredoxin-related transmembrane protein 3 coding TMX3 gene in 18q22.

TABLE 5

Results from GWAS of suicide behaviour severity in the bipolar disorder sample. Allele 2 is the test allele.

| | | Sample CA2 | | |
|---|---|---|---|---|
| SNP | CHR | BETA | P | Allele1:Allele2 |
| rs2610025 | 8q23-q24 | −0.03547 | 0.001265 | C:A |
| rs7075553 | 10p11 | 0.0379 | 0.000803 | G:A |
| rs980117 | 10p11 | 0.03705 | 0.001049 | G:T |
| rs1832048 | 10p11 | 0.03727 | 0.000961 | A:C |
| rs1413977 | 10p11 | 0.03727 | 0.000961 | A:T |
| rs2184486 | 10p11 | 0.03727 | 0.000961 | T:C |
| rs7899433 | 10p11 | 0.03727 | 0.000961 | G:C |
| rs7899442 | 10p11 | 0.03727 | 0.000961 | G:A |
| rs7899680 | 10p11 | 0.03727 | 0.000961 | C:T |
| rs7078469 | 10p11 | 0.03727 | 0.000961 | A:C |

TABLE 5-continued

Results from GWAS of suicide behaviour severity in the bipolar disorder sample. Allele 2 is the test allele.

| | | Sample CA2 | | |
|---|---|---|---|---|
| SNP | CHR | BETA | P | Allele1:Allele2 |
| rs7079041 | 10p11 | 0.03727 | 0.000961 | G:A |
| rs7900825 | 10p11 | 0.03727 | 0.000961 | T:G |
| rs7914502 | 10p11 | 0.03623 | 0.03623 | T:C |
| rs720903 | 10p11 | −0.0429 | 0.03839 | A:T |

TABLE 6

Results from GWAS of suicide attempt in the bipolar disorder sample. Allele 2 is the test allele.

| | | Sample CA2 | | |
|---|---|---|---|---|
| SNP | CHR | Odds Ratio | P | Allele1:Allele2 |
| rs10448042 | 8q12-q21 | 1.816 | 0.01003 | A:G |
| rs10448044 | 8q12-q21 | 1.854 | 0.007873 | T:C |
| rs3851150 | 18q22 | 2.108 | 0.002361 | A:C |
| rs7244261 | 18q22 | 2.125 | 0.002086 | C:T |

Discussion

We report here interesting findings in two chromosomal regions from the first GWAS of suicide severity in BD patients. The region of interest on chromosome 8 is located 5' of the PENK gene that codes for an opioid polypeptide hormone proenkephalin. The PENK protein is expressed in most tissues including the central nervous system, with the highest expression in the caudate nucleus, putamen, central nucleus, and nucleus accumbens. Genetic mouse models have implicated PENK in regulating anxious and freezing behaviours. It may also play a role in regulating anxious and depressive behaviours after exposure to stress. Consequently, adding information on childhood trauma history may help to reduce the heterogeneity within the samples and address part of the mixed findings reported thus far. The region of interest on chromosome 10 encompasses ITGB1 and CCDC7. Huang et al showed in 2006 that conditional genetic ablation of the ITGB1 gene resulted in defective cortical lamination during development and deficient long-term potentiation. The function of CCDC7 is unknown, but its expression in the brain appears to be highest in the globus pallidus and corpus callosum according to the Allen Brain Atlas (See Shen et al, 2012).

Two chromosomal regions of interest were also found from the GWAS of suicide attempt in BD patients. The first was localized to 8q12-q21 about 400 kb upstream of the IL7 gene. Interleukin 7 has been shown to augment neuronal differentiation (Macia et al, 2010; Moors et al, 2010). It is expressed in the brain, with the highest expression in the hypothalamus. Its expression in the hypothalamus also matches its purported role in the regulation of feeding behaviour and body weight. The second was about 150 kb downstream of the TMX3 gene in 18q22. TMX3 has the highest expression in the hypothalamus, but its role in this part of the brain has not been explored.

The effect of psychotropic medication is an important confounder in suicide genetic studies. Three GWAS of treatment-enhanced or -emergent suicidality have been carried out in large major depression samples (Laje et al, 2009; Menke et al, 2012; Perroud et al, 2012). However, it is important to note that high suicidality is often an exclusion criteria for these longitudinal studies due to safety issues, making these study samples somewhat biased for the purpose of studying the lifetime history of suicide attempt and limited in their comparability with other studies on suicide attempt history. It is important to note that the suicide severity phenotype examined corresponds to current or the most serious depressive episode, while previous GWASs of suicide (Perlis et al, 2010; Willour et al, 2012) were in regards to lifetime history of suicide attempt. Although most suicide attempts in bipolar disorder occur during the depressive phase, a few mixed-slate suicide attempters might have been missed (Valtonen et al. 2007). In addition, for the analysis of suicide attempt, the suicide attempter cases would have included individuals who have a history of non-suicidal self-injury, as non-suicidal self-injury can be a strong predictor of future suicide attempt (Horwitz et al, 2014; Victor & Klonsky, 2014). Thus, the findings may not be directly comparable to previously published GWASs.

In summary, a number of associations were identified, including regions on chromosomes 8 and 10. These findings demonstrate that many gene variants contribute collectively to the risk for suicidal behaviour severity in BD. We undertook a further analysis of the data to identify panels of markers that, collectively, provide a stronger association with that risk. This work is described in Example 2 below.

Example 2

We analyzed 237 bipolar disorder patients (Sample CA2/GBP) from the Centre for Addiction and Mental Health in Toronto, Canada. Details on the sample are described above. Demographic information on the sample are shown in Table 7 below. The participants were of self-reported European ancestry and at least 18 years old at time of enrolment. Their diagnoses for bipolar disorder according to DSM-IV and ICD-10 criteria were confirmed using the Schedules for Clinical Assessment in Neuropsychiatry (SCAN). Participants who had mood-incongruent psychotic symptoms, intravenous drug dependence, reported intravenous drug use, manic episodes only in concurrence with or as a result of alcohol, substance dependence or abuse, medication, or medical illnesses were excluded from the analysis.

Genotypes for Markers A, B, C, D, and E were determined with the Illumina Sentrix Human Hap550 Beadchip (Illumina Inc., San Diego, Calif. USA) at Illumina Inc. (San Diego, Calif., USA) or the Genome Quebec facility (Montreal, Quebec, Canada) and are also described in our earlier application, PCT/CA2014/051257 filed 23 Dec. 2014.

Genotypes for Markers F, G, H, I, J, and K were determined through imputation using IMPUTE2 (Howie et al, 2012) after prephasing in SHAPEIT2 (Delaneau et al. 2013) with 1000 Genome Project (Abecasis et al. 2010) b37 genotypes as reference. Then we converted the format to PLINK using GTOOL (Genetics Software Suite, © 2007, The University of Oxford) with a genotype call threshold of 0.9. Suicide Severity was assessed using item 6.011 Suicide Severity of the SCAN as follows: 0 for non-suicidal, 1 for deliberately considering suicide or self-harm, 2 for injuring self or making an attempt without serious consequences; 3 for serious self-harm or attempt; 4 for an attempt at suicide designed to be lethal. We performed linear regression on log-transformed suicide severity scores for the sample in SPSS. We included age, sex, past alcohol use disorder, the number of depressive episodes, and the first two components from the MDS analysis as covariates. Genotypes were coded as follows: 1 for homozygotes for risk allele (high-risk genotype), 0.5 for heterozygotes (intermediate-risk genotype), and 0 for homozygotes for the protective allele (low-risk genotype). Table 8 shows the identity of the markers included in the study and the genotype risk scores for each.

TABLE 7

Demographic information on the bipolar disorder sample.

| | |
|---|---|
| Bipolar_Disorder_Sample | CA2/GBP |
| Site | CAMH |
| Number_of_Cases | 237 |
| Genotyping_platform | Illumina Sentrix Human Hap550 Beadchip |
| Suicide_Measure | SCAN 6.011 |
| Average_Age (Std_Dev) | 42.78 +/− 12.45 |
| Sex_Ratio (% Male) | 0.41 |

TABLE 8

Genetic markers for severe suicidal behavior

| | SNP | CHR | BP | Minor allele | Genotype Risk Scores | Phenotype |
|---|---|---|---|---|---|---|
| A | rs2491144 | 1 | 31327011 | A | GC 1/GA 0.5/AA 0 | SuicSev |
| B | rs9315639 | 13 | 39544663 | T | CC 1/CT 0.5/TT 0 | SuicSev |
| C | rs11082138 | 18 | 36998210 | C | CC 1/CT 0.5/TT 0 | SuicSev |
| D | rs11697517 | 20 | 48409772 | T | TT 1/CT 0.5/CC 0 | SuicSev |
| E | rs2186437 | 21 | 25870353 | A | CC 1/CA 0.5/AA 0 | SuicSev |
| F | rs2610025 | 8 | 57505313 | A | CC 1/CA 0.5/AA 0 | SuicSev |
| G | rs10448044 | 8 | 80103432 | C | CC 1/CT 0.5/TT 0 | SuicSev |
| H | rs7079041 | 10 | 32993268 | A | AA 1/AG 0.5/GG 0 | SuicSev |
| I | rs720903 | 10 | 36589479 | A | AA 1/AT 0.5/TT 0 | SuicSev |
| J | rs10483836 | 14 | 72001614 | G | GG 1/GT 0.5/TT 0 | SuicSev |
| K | rs7244261 | 18 | 66214696 | T | TT 1/CT 0.5/CC 0 | SuicSev |

Boxplots showing raw suicide severity scores (y-axis) versus genotype risk score for various marker combinations (on the x-axis) are shown in FIGS. 6 to 33. As discussed above, the suicide severity scores on the y-axis indicate likelihood of severe suicidal behavior as assessed using the Suicide Severity item of the Schedules of Clinical Assessment in Neuropsychiatry. An increased risk of suicide attempt is indicated by a score on the y-axis above 1.0. Adjusted r-squared values and the ANOVA p-values are shown in the data tables below corresponding to each boxplot. The r-squared value indicates how much of the observed variance is explained by the indicated markers. Thus, in Table 9 below, 5.8% of the variance is explained by markers A-C.

The figures and box plots are labeled with the letters corresponding to the SNPs shown in Table 8 above. Thus, for example, "AC" indicates the additive genotype risk scores from Markers A and C and "BCD" indicates the additive genotype risk scores from Markers B, C, and D. The "Number of Individuals" column in the tables below indicates the number of individuals having the indicated genotype risk score and the corresponding percentage of total individuals is indicated in parentheses. The column labeled "Suicide Severity Group" is based on the median suicide severity (raw 6.011) scores for the additive genotype risk scores from the indicated markers.

TABLE 9

AC p = 0.004; $r^2$ = 0.058

| Genotype risk score | Number of individuals | Suicide Severity Group |
|---|---|---|
| 0 | 13 (0.055) | Low |
| 0.5 | 78 (0.329) | Intermediate |
| 1 | 118 (0.498) | Intermediate |
| 1.5 | 27 (0.114) | Intermediate |
| 2 | 1 (0.004) | Intermediate |

TABLE 10

BC p = 0.005; $r^2$ = 0.055

| Genotype risk score | Number of individuals | Suicide Severity Group |
|---|---|---|
| 0 | 23 (0.097) | Intermediate |
| 0.5 | 100 (0.422) | Intermediate |
| 1 | 95 (0.401) | Intermediate |
| 1.5 | 19 (0.080) | High |

TABLE 11

CD p = 2.75 × $10^{-4}$; $r^2$ = 0.085

| Genotype risk score | Number of individuals | Suicide Severity Group |
|---|---|---|
| 0 | 75 (0.316) | Low |
| 0.5 | 109 (0.460) | Intermediate |
| 1 | 47 (0.198) | Intermediate |
| 1.5 | 6 (0.025) | Intermediate |

TABLE 12

ACD p = 2.21 × 10$^{-4}$; r$^2$ = 0.087

| Genotype risk score | Number of individuals | Suicide Severity Group |
|---|---|---|
| 0 | 4 (0.017) | Low |
| 0.5 | 45 (0.190) | Low |
| 1 | 77 (0.325) | Intermediate |
| 1.5 | 74 (0.312) | Intermediate |
| 2 | 33 (0.139) | Intermediate |
| 2.5 | 4 (0.017) | Intermediate |

TABLE 13

BCD p = 2.77 × 10$^{-4}$; r$^2$ = 0.085

| Genotype risk score | Number of individuals | Suicide Severity Group |
|---|---|---|
| 0 | 9 (0.038) | Low |
| 0.5 | 60 (0.253) | Intermediate |
| 1 | 71 (0.300) | Intermediate |
| 1.5 | 72 (0.304) | Intermediate |
| 2 | 22 (0.093) | Intermediate |
| 2.5 | 3 (0.013) | High |

TABLE 14

ABCDE p = 3.17 × 10$^{-5}$; r$^2$ = 0.105

| Genotype risk score | Number of individuals | Suicide Severity Group |
|---|---|---|
| 0.5 | 2 (0.008) | Low |
| 1 | 4 (0.017) | Low |
| 1.5 | 17 (0.072) | Low |
| 2 | 41 (0.173) | Intermediate |
| 2.5 | 57 (0.241) | Intermediate |
| 3 | 61 (0.257) | Intermediate |
| 3.5 | 42 (0.177) | Intermediate |
| 4 | 11 (0.046) | High |
| 4.5 | 2 (0.008) | High |

TABLE 15

FH p = 0.001; r$^2$ = 0.076

| Genotype risk score | Number of individuals | Suicide Severity Group |
|---|---|---|
| 0 | 23 (0.097) | Low |
| 0.5 | 79 (0.333) | Intermediate |
| 1.0 | 80 (0.338) | Intermediate |
| 1.5 | 47 (0.198) | Intermediate |
| 2.0 | 8 (0.034) | High |

TABLE 16

GH p = 0.008; r2 = 0.050

| Genotype risk score | Number of individuals | Suicide Severity Group |
|---|---|---|
| 0 | 61 (0.257) | Intermediate |
| 0.5 | 98 (0.414) | Intermediate |
| 1.0 | 59 (0.249) | Intermediate |
| 1.5 | 19 (0.080) | High |

TABLE 17

FGH p = 4.73 × 10$^{-4}$; r$^2$ = 0.080

| Genotype risk score | Number of individuals | Suicide Severity Group |
|---|---|---|
| 0 | 17 (0.072) | Low |
| 0.5 | 54 (0.228) | Intermediate |
| 1.0 | 74 (0.312) | Intermediate |
| 1.5 | 57 (0.241) | Intermediate |
| 2.0 | 29 (0.122) | High |
| 2.5 | 6 (0.025) | High |

TABLE 18

FHI p = 1.51 × 10$^{-4}$; r$^2$ = 0.090

| Genotype risk score | Number of individuals | Suicide Severity Group |
|---|---|---|
| 0 | 19 (0.080) | Low |
| 0.5 | 67 (0.283) | Intermediate |
| 1.0 | 83 (0.350) | Intermediate |
| 1.5 | 51 (0.215) | Intermediate |
| 2.0 | 16 (0.068) | High |
| 2.5 | 1 (0.004) | High |

TABLE 19

FHK p = 2.33 × 10$^{-4}$; r$^2$ = 0.086

| Genotype risk score | Number of individuals | Suicide Severity Group |
|---|---|---|
| 0 | 18 (0.076) | Intermediate |
| 0.5 | 57 (0.241) | Intermediate |
| 1.0 | 74 (0.312) | Intermediate |
| 1.5 | 60 (0.253) | Intermediate |
| 2.0 | 19 (0.080) | High |
| 2.5 | 8 (0.034) | High |
| 3.0 | 1 (0.004) | High |

TABLE 20

GHJ p = 0.005; r$^2$ = 0.056

| Genotype risk score | Number of individuals | Suicide Severity Group |
|---|---|---|
| 0 | 33 (0.139) | Intermediate |
| 0.5 | 86 (0.363) | Intermediate |
| 1.0 | 65 (0.274) | Intermediate |
| 1.5 | 42 (0.177) | Intermediate |
| 2.0 | 10 (0.042) | High |
| 2.5 | 1 (0.004) | High |

TABLE 21

GHK p = 0.002; r$^2$ = 0.064

| Genotype risk score | Number of individuals | Suicide Severity Group |
|---|---|---|
| 0 | 43 (0.181) | Intermediate |
| 0.5 | 79 (0.333) | Intermediate |
| 1.0 | 71 (0.300) | Intermediate |
| 1.5 | 31 (0.131) | High |
| 2.0 | 11 (0.046) | High |
| 2.5 | 2 (0.008) | High |

TABLE 22

HJK $p = 0.003$; $r^2 = 0.061$

| Genotype risk score | Number of individuals | Suicide Severity Group |
|---|---|---|
| 0 | 44 (0.186) | Intermediate |
| 0.5 | 73 (0.308) | Intermediate |
| 1.0 | 69 (0.291) | Intermediate |
| 1.5 | 40 (0.169) | High |
| 2.0 | 11 (0.046) | High |

TABLE 23

FGHI $p = 1.26 \times 10^{-4}$; $r^2 = 0.092$

| Genotype risk score | Number of individuals | Suicide Severity Group |
|---|---|---|
| 0 | 15 | Low |
| 0.5 | 42 | Intermediate |
| 1.0 | 77 | Intermediate |
| 1.5 | 60 | Intermediate |
| 2.0 | 32 | High |
| 2.5 | 8 | High |
| 3.0 | 3 | High |

TABLE 24

FGHJ $p = 2.86 \times 10^{-4}$; $r^2 = 0.084$

| Genotype risk score | Number of individuals | Suicide Severity Group |
|---|---|---|
| 0 | 11 | Low |
| 0.5 | 37 | Intermediate |
| 1.0 | 61 | Intermediate |
| 1.5 | 66 | Intermediate |
| 2.0 | 38 | Intermediate |
| 2.5 | 21 | High |
| 3.0 | 2 | High |
| 3.5 | 1 | High |

TABLE 25

FGHK $p = 1.86 \times 10^{-4}$; $r^2 = 0.088$

| Genotype risk score | Number of individuals | Suicide Severity Group |
|---|---|---|
| 0 | 13 | Intermediate |
| 0.5 | 42 | Intermediate |
| 1.0 | 64 | Intermediate |
| 1.5 | 60 | Intermediate |
| 2.0 | 31 | High |
| 2.5 | 23 | High |
| 3.0 | 3 | High |
| 3.5 | 1 | High |

TABLE 26

FGJK $p = 0.003$; $r^2 = 0.060$

| Genotype risk score | Number of individuals | Suicide Severity Group |
|---|---|---|
| 0 | 20 | Intermediate |
| 0.5 | 50 | Intermediate |
| 1.0 | 54 | Intermediate |
| 1.5 | 66 | Intermediate |
| 2.0 | 34 | High |
| 2.5 | 9 | High |
| 3.0 | 3 | High |
| 3.5 | 1 | High |

TABLE 27

FHIJ $p = 1.38 \times 10^{-4}$; $r^2 = 0.091$

| Genotype risk score | Number of individuals | Suicide Severity Group |
|---|---|---|
| 0 | 14 | Low |
| 0.5 | 42 | Intermediate |
| 1.0 | 70 | Intermediate |
| 1.5 | 71 | Intermediate |
| 2.0 | 27 | Intermediate |
| 2.5 | 12 | High |
| 3.0 | 1 | High |

TABLE 28

FHJK $p = 1.87 \times 10^{-4}$; $r^2 = 0.088$

| Genotype risk score | Number of individuals | Suicide Severity Group |
|---|---|---|
| 0 | 13 | Intermediate |
| 0.5 | 42 | Intermediate |
| 1.0 | 57 | Intermediate |
| 1.5 | 60 | Intermediate |
| 2.0 | 44 | High |
| 2.5 | 17 | High |
| 3.0 | 4 | High |

TABLE 29

GHIJ $p = 0.001$; $r^2 = 0.069$

| Genotype risk score | Number of individuals | Suicide Severity Group |
|---|---|---|
| 0 | 26 | Intermediate |
| 0.5 | 77 | Intermediate |
| 1.0 | 71 | Intermediate |
| 1.5 | 45 | Intermediate |
| 2.0 | 15 | High |
| 2.5 | 2 | High |
| 3.0 | 1 | High |

TABLE 30

GHJK $p = 0.001$; $r^2 = 0.076$

| Genotype risk score | Number of individuals | Suicide Severity Group |
|---|---|---|
| 0 | 34 | Intermediate |
| 0.5 | 73 | Intermediate |
| 1.0 | 75 | Intermediate |
| 1.5 | 39 | Intermediate |
| 2.0 | 11 | High |
| 2.5 | 3 | High |
| 3.0 | 2 | High |

TABLE 31

GHJK p = 0.001; $r^2$ = 0.070

| Genotype risk score | Number of individuals | Suicide Severity Group |
|---|---|---|
| 0 | 28 | Intermediate |
| 0.5 | 60 | Intermediate |
| 1.0 | 64 | Intermediate |
| 1.5 | 54 | Intermediate |
| 2.0 | 24 | High |
| 2.5 | 6 | High |
| 3.0 | 1 | High |

TABLE 32

GIJK p = 0.012; $r^2$ = 0.046

| Genotype risk score | Number of individuals | Suicide Severity Group |
|---|---|---|
| 0 | 52 | Intermediate |
| 0.5 | 64 | Intermediate |
| 1.0 | 84 | Intermediate |
| 1.5 | 25 | High |
| 2.0 | 9 | High |
| 2.5 | 2 | High |
| 3.0 | 1 | High |

TABLE 33

HIJK p = 0.001; $r^2$ = 0.075

| Genotype risk score | Number of individuals | Suicide Severity Group |
|---|---|---|
| 0 | 35 | Intermediate |
| 0.5 | 67 | Intermediate |
| 1.0 | 75 | Intermediate |
| 1.5 | 42 | Intermediate |
| 2.0 | 15 | High |
| 2.5 | 3 | High |

TABLE 34

FGHIJ p = 7.44 × $10^{-5}$; $r^2$ = 0.097

| Genotype risk score | Number of individuals | Suicide Severity Group |
|---|---|---|
| 0 | 10 | Low |
| 0.5 | 30 | Intermediate |
| 1.0 | 55 | Intermediate |
| 1.5 | 71 | Intermediate |
| 2.0 | 41 | Intermediate |
| 2.5 | 24 | High |
| 3.0 | 4 | High |
| 3.5 | 1 | High |
| 4.0 | 1 | High |

TABLE 35

FGIJK p = 0.001; $r^2$ = 0.071

| Genotype risk score | Number of individuals | Suicide Severity Group |
|---|---|---|
| 0 | 17 | Low |
| 0.5 | 46 | Intermediate |
| 1.0 | 44 | Intermediate |
| 1.5 | 77 | Intermediate |
| 2.0 | 34 | Intermediate |
| 2.5 | 13 | High |
| 3.0 | 4 | High |
| 3.5 | 1 | High |
| 4.0 | 1 | High |

TABLE 36

FHIJK p = 4.45 × $10^{-5}$; $r^2$ = 0.102

| Genotype risk score | Number of individuals | Suicide Severity Group |
|---|---|---|
| 0 | 11 | Low |
| 0.5 | 34 | Intermediate |
| 1.0 | 57 | Intermediate |
| 1.5 | 61 | Intermediate |
| 2.0 | 45 | Intermediate |
| 2.5 | 23 | Intermediate |
| 3.0 | 4 | High |
| 3.5 | 2 | High |

The data indicate that certain combinations of markers are much more informative at assessing a subject's risk of severe suicidal behavior. As an example, for Table 14, individuals with genotype risk scores of 1.5 or less, based on the number of risk alleles they possess for Markers A, B, C, D, and E, were classified as being at low risk for SSB. Intervention as usual with monitoring on a regular basis would be suggested for these individuals. For individuals with genotype risk scores of 2 to 3.5, they were identified as being at intermediate risk for SSB, and their interventions would include more frequent visits and monitoring, medication adjustments, augmentation with other therapies (including but not limited to psychotherapies, cognitive behavioral therapy, and brain stimulation). For individuals with genotype risk scores of 4 or above, they were identified as being at high risk for SSB. For these high-risk individuals, in addition to interventions considered for intermediate-risk individuals, hospitalization that might include higher levels of observations would be contemplated. Treating physicians would also advise family members and alert other caregivers (for example, community nurses, social workers, and mental health workers) to increase vigilance for these high-risk individuals.

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method for treating a subject at risk of severe suicidal behavior (SSB), the method comprising generating an SSB risk assessment of the subject selected from high, intermediate, and low based upon the subject's genotype for a plurality of single nucleotide polymorphisms (SNPs), the plurality consisting of each SNP in at least one panel of SNPs selected from the group consisting of Panels 1-22:

| Panel # | SNPs (human) | Genotype risk score | Suicide Severity Group |
|---|---|---|---|
| 1 | F, H | 0 | Low |
|   |   | 0.5 | Intermediate |
|   |   | 1.0 | Intermediate |
|   |   | 1.5 | Intermediate |
|   |   | 2.0 | High |
| 2 | G, H | 0 | Intermediate |
|   |   | 0.5 | Intermediate |
|   |   | 1.0 | Intermediate |
|   |   | 1.5 | High |
| 3 | F, G, H | 0 | Low |
|   |   | 0.5 | Intermediate |
|   |   | 1.0 | Intermediate |
|   |   | 1.5 | Intermediate |
|   |   | 2.0 | High |
|   |   | 2.5 | High |
| 4 | F, H, I | 0 | Low |
|   |   | 0.5 | Intermediate |
|   |   | 1.0 | Intermediate |
|   |   | 1.5 | Intermediate |
|   |   | 2.0 | High |
|   |   | 2.5 | High |
| 5 | F, H, K | 0 | Intermediate |
|   |   | 0.5 | Intermediate |
|   |   | 1.0 | Intermediate |
|   |   | 1.5 | Intermediate |
|   |   | 2.0 | High |
|   |   | 2.5 | High |
|   |   | 3.0 | High |
| 6 | G, H, J | 0 | Intermediate |
|   |   | 0.5 | Intermediate |
|   |   | 1.0 | Intermediate |
|   |   | 1.5 | Intermediate |
|   |   | 2.0 | High |
|   |   | 2.5 | High |
| 7 | G, H, K | 0 | Intermediate |
|   |   | 0.5 | Intermediate |
|   |   | 1.0 | Intermediate |
|   |   | 1.5 | High |
|   |   | 2.0 | High |
|   |   | 2.5 | High |
| 8 | H, J, K | 0 | Intermediate |
|   |   | 0.5 | Intermediate |
|   |   | 1.0 | Intermediate |
|   |   | 1.5 | High |
|   |   | 2.0 | High |
| 9 | F, G, H, I | 0 | Low |
|   |   | 0.5 | Intermediate |
|   |   | 1.0 | Intermediate |
|   |   | 1.5 | Intermediate |
|   |   | 2.0 | High |
|   |   | 2.5 | High |
|   |   | 3.0 | High |
| 10 | F, G, H, J | 0 | Low |
|   |   | 0.5 | Intermediate |
|   |   | 1.0 | Intermediate |
|   |   | 1.5 | Intermediate |
|   |   | 2.0 | Intermediate |
|   |   | 2.5 | High |
|   |   | 3.0 | High |
|   |   | 3.5 | High |
| 11 | F, G, H, K | 0 | Intermediate |
|   |   | 0.5 | Intermediate |
|   |   | 1.0 | Intermediate |
|   |   | 1.5 | Intermediate |
|   |   | 2.0 | High |
|   |   | 2.5 | High |
|   |   | 3.0 | High |
|   |   | 3.5 | High |
| 12 | F, G, J, K | 0 | Intermediate |
|   |   | 0.5 | Intermediate |
|   |   | 1.0 | Intermediate |
|   |   | 1.5 | Intermediate |
|   |   | 2.0 | High |
|   |   | 2.5 | High |
|   |   | 3.0 | High |
|   |   | 3.5 | High |
| 13 | F, H, I, J | 0 | Low |
|   |   | 0.5 | Intermediate |
|   |   | 1.0 | Intermediate |
|   |   | 1.5 | Intermediate |
|   |   | 2.0 | Intermediate |
|   |   | 2.5 | High |
|   |   | 3.0 | High |
| 14 | F, H, J, K | 0 | Intermediate |
|   |   | 0.5 | Intermediate |
|   |   | 1.0 | Intermediate |
|   |   | 1.5 | Intermediate |
|   |   | 2.0 | High |
|   |   | 2.5 | High |
|   |   | 3.0 | High |
| 15 | G, H, I, J | 0 | Intermediate |
|   |   | 0.5 | Intermediate |
|   |   | 1.0 | Intermediate |
|   |   | 1.5 | Intermediate |
|   |   | 2.0 | High |
|   |   | 2.5 | High |
|   |   | 3.0 | High |
| 16 | G, H, I, K | 0 | Intermediate |
|   |   | 0.5 | Intermediate |
|   |   | 1.0 | Intermediate |
|   |   | 1.5 | Intermediate |
|   |   | 2.0 | High |
|   |   | 2.5 | High |
|   |   | 3.0 | High |

-continued

| Panel # | SNPs (human) | Genotype risk score | Suicide Severity Group |
|---|---|---|---|
| 17 | G, H, J, K | 0 | Intermediate |
|  |  | 0.5 | Intermediate |
|  |  | 1.0 | Intermediate |
|  |  | 1.5 | Intermediate |
|  |  | 2.0 | High |
|  |  | 2.5 | High |
|  |  | 3.0 | High |
| 18 | G, I, J, K | 0 | Intermediate |
|  |  | 0.5 | Intermediate |
|  |  | 1.0 | Intermediate |
|  |  | 1.5 | High |
|  |  | 2.0 | High |
|  |  | 2.5 | High |
|  |  | 3.0 | High |
| 19 | H, I, J, K | 0 | Intermediate |
|  |  | 0.5 | Intermediate |
|  |  | 1.0 | Intermediate |
|  |  | 1.5 | Intermediate |
|  |  | 2.0 | High |
|  |  | 2.5 | High |
| 20 | F, G, H, I, J | 0 | Low |
|  |  | 0.5 | Intermediate |
|  |  | 1.0 | Intermediate |
|  |  | 1.5 | Intermediate |
|  |  | 2.0 | Intermediate |
|  |  | 2.5 | High |
|  |  | 3.0 | High |
|  |  | 3.5 | High |
|  |  | 4.0 | High |
| 21 | F, G, I, J, K | 0 | Low |
|  |  | 0.5 | Intermediate |
|  |  | 1.0 | Intermediate |
|  |  | 1.5 | Intermediate |
|  |  | 2.0 | Intermediate |
|  |  | 2.5 | High |
|  |  | 3.0 | High |
|  |  | 3.5 | High |
|  |  | 4.0 | High |
| 22 | F, H, I, J, K | 0 | Low |
|  |  | 0.5 | Intermediate |
|  |  | 1.0 | Intermediate |
|  |  | 1.5 | Intermediate |
|  |  | 2.0 | Intermediate |
|  |  | 2.5 | Intermediate |
|  |  | 3.0 | High |
|  |  | 3.5 | High | wherein SNPs F-K are identified by SEQ ID NOS 1-6, respectively; and administering to the subject having an SSB risk assessment of "high" one or more medications selected from the group consisting of a selective serotonin reuptake inhibitor (SSRI), an irreversible monoamine oxidase inhibitor (MAOI), eicosapentaenoic acid (EPA), a COX-2 inhibitor, and lithium; and administering to the subject having an SSB risk assessment of "intermediate" or "low" a single medication selected from the group consisting of an SSRI inhibitor, an irreversible MAOI inhibitor, EPA, a COX-2 inhibitor, and lithium.

2. The method of claim 1, further comprising assigning, by at least one processor, a genetic risk score to each genotype of the plurality of SNPs.

3. The method of claim 2, further comprising generating, by at least one processor, a total genetic risk score for the subject based on a sum of genetic risk scores of the plurality of SNPs.

4. The method of claim 3, further comprising outputting an indication of the subject's SSB risk assessment.

5. The method of claim 4, wherein the indication is an audio, visual or textual indication, or any combination of the foregoing.

6. The method of claim 4, wherein the outputting is to a graphical user interface (GUI).

7. The method of claim 4, wherein the subject's genotype is received directly from equipment used to determine the genotype or the subject's genotype is input by a user.

8. The method of claim 1, further comprising determining or receiving the subject's genotype.

9. The method of claim 8, further comprising obtaining a biological sample from the subject prior to determining or receiving the subject's genotype.

10. The method of claim 9, wherein the biological sample is blood or saliva.

11. The method of claim 1, wherein the at least one panel of SNPs is selected from panel 2, 9, 15, 17, 19 and 20.

12. The method of claim 1, wherein the at least one panel of SNPs is selected from panel 9, 15, 17, and 19.

13. The method of claim 12, wherein a total genetic risk score of 2 or more indicates the subject is at high risk of SSB.

14. The method of claim 1, wherein the subject is a human psychiatric patient.

* * * * *